(12) United States Patent
Fulga et al.

(10) Patent No.: US 9,404,084 B2
(45) Date of Patent: Aug. 2, 2016

(54) REGULATING STEM CELLS

(75) Inventors: Valentin Fulga, Toronto (CA); Yael Porat, Hod Hasharon (IL); Svetlana Porozov, Rehovot (IL); Daphna Shimoni-Zalk, Nes Ziona (IL)

(73) Assignee: KWALATA TRADING LIMITED, Nicosia (CY)

( * ) Notice: Subject to any disclaimer, the term of this patent is extended or adjusted under 35 U.S.C. 154(b) by 1204 days.

(21) Appl. No.: 11/820,975

(22) Filed: Jun. 20, 2007

(65) Prior Publication Data

US 2008/0317719 A1 Dec. 25, 2008

(51) Int. Cl.
*C12N 5/00* (2006.01)
*C12N 5/0789* (2010.01)

(52) U.S. Cl.
CPC ........ *C12N 5/0647* (2013.01); *C12N 2501/165* (2013.01); *C12N 2501/91* (2013.01)

(58) Field of Classification Search
None
See application file for complete search history.

(56) References Cited

U.S. PATENT DOCUMENTS

| | | | |
|---|---|---|---|
| 5,840,502 A | 11/1998 | Vlasselaer | |
| 6,810,286 B2 | 10/2004 | Donovan et al. | |
| 7,015,037 B1 | 3/2006 | Furcht | |
| 2002/0151056 A1 | 10/2002 | Sasai et al. | |
| 2003/0044977 A1 | 3/2003 | Sakuragawa et al. | |
| 2004/0136973 A1 | 7/2004 | Huberman et al. | |
| 2005/0003534 A1 | 1/2005 | Huberman et al. | |
| 2005/0260158 A1 | 11/2005 | Huberman et al. | |
| 2008/0220466 A1 | 9/2008 | Fulga | |
| 2008/0317719 A1 | 12/2008 | Fulga | |

FOREIGN PATENT DOCUMENTS

| | | |
|---|---|---|
| WO | WO87/06233 | 10/1987 |
| WO | 01/30981 | 5/2001 |
| WO | 03/055989 A1 | 7/2003 |
| WO | WO 03/078610 A1 | 9/2003 |
| WO | WO 2004/055989 A2 | 7/2004 |
| WO | 2005/120090 | 9/2005 |
| WO | 2005120090 | 12/2005 |

OTHER PUBLICATIONS

Reinecke et al J Cell Mol Cell Cardiology, 34, 2002, 241-249.*
Murry et al. Nature vol. 428 2004. 664-668.*
Evans MJ. and Kaufman M.H. (1981), "Establishment in Culture of Pluripotential Cells From Mouse Embryos", Nature 292: 154-156.
Donovan PJ. and Gearhart J. (2001) "The End of the Beginning for Pluripotent Stem Cells" Nature 414:92-97.
Spralding A. et al.,"Stem Cells Find Their Niche", Nature 414:98-104.
Weissman I.L. et al.,"Stem and Progenitor Cells: Origins, Phenotypes, Lineage Commitments, and Transdifferentiations", Annu. Rev. Cell. Dev. Biol. 17:387-403.
Weissman L.L.,(2000)"Stem, Cells: Unit of Development, Units of Regeneration, and Units in Evolution", Cell 100: 157-68.
Cheng A., Wang. S., Cai J., Rao MS, Mattson MP, (2003),"Nitric Oxide Acts in a Positive Feedback Loop With BDNF to Regulate Neural Progenitor Cell Proliferation and Differentiation in the Mammalian Brain," Dev Biol. 258(2):319-33.
Cousin B, Andre M, Arnaud E, Penicaud L, Casteilla L (2003),"Reconstitution of Lethally Irradiated Mice by Cells Isolated From Adipose Tissue" Biochem Biophys Res Cornmun. 301(4): 1016-22.
Anderson DJ., Gage, F.H., and Weissman, LL. (2001)."Can Stem Cells Cross Lineage Boundaries?" Nat. Med. 7:393-395.
Robey P.G. (2000),"Stem Cells Near the Century Mark" J. Clin. Invest. 105:1489-1491.
Eisenberg LM, Burns L, Eisenberg CA (2003),"Hematopoietic Cells From Bone Marrow Have the Potential to Differentiate Into Cardiomyocytes In Vitro" Anat Rec. 274A(1):870-882.
Karl J.L., Fernandes Ian A., McKenzie, Pleasantine Mill et al. (2004),"A Dermal Niche for Multipotent Adult Skin-Derived Precursor Cells," Nature Cell Biology Published online: Nov. 1, 2004, DOI: 10.1038/ncbl 181.
Jackson KA, Mi T, Goodell MA (1999),"Hematopoietic Potential of Stem Cells Isolated From Murine Skeletal Muscle," Proc Natl Acad Sci USA 96(25):14482-14486.
Brazelton TR, Rossi FM, Keshet GI, Blau HM (2000),"From Marrow to Brain: Expression of Neuronal Phenotypes in Adult Mice," Science 290(5497): 1775-1779.
Bjornson CR, Rietze RL, Reynolds BA, Magli MC, Veseovi AL (1999),"Turning Brain Into Blood: A Hematopoietic Fate Adopted by Adult Neural Stem Cells In Vivo,", Science 283(5401):534-537.
Slack, J.M. (2000)"Stem Cells in Epithelial Tissues," Science 287: 1431-1433.
Ferrari G., Cusella-De Angelis G., Coletta M., Paolucci E., Stornaiuolo A., Cossu G., and Mavilio F. (1998),"Muscle Regeneration by Bone Marrow-Derived Myogenic Progenitors", Science 279: 528-530.
Lagasse E, Connors H, Al-Dhalimy M, Retisma M, Osborne L, Wang X, Finegold M, Weissman IL, Grompe M (2000),"Purified Hematopoietic Stem Cells Can Differentiate Into Hepatocytes In Vivo" Nat Med. 6:1229-1234.
Hirschi K.K., and Goodell, M.A. (2002),"Hematopoietic, Vascular and Cardiac Fates of Bone Marrow-Derived Stem Cells," Gene Therap. 9:648-652.

(Continued)

*Primary Examiner* — Blaine Lankford
(74) *Attorney, Agent, or Firm* — Nixon Peabody LLP; David S. Resnick; Leena H. Karttunen Contarino

(57) ABSTRACT

A method is provided, including in vitro stimulating an initiating cell population (ICP) of at least 5 million cells that have a density of less than 1.072 g/ml, and at least 1% of which are CD34+CD45−/dim, to differentiate into a progenitor/precursor cell population (PCP). A method is provided, including in vitro stimulating an initiating cell population (ICP) of at least ten thousand cells that have a density of less than 1.072 g/ml to differentiate into a progenitor/precursor cell population (PCP). A method is provided, including separating lower density cells from higher density cells, the lower density cells defining an initiating cell population (ICP), and in vitro stimulating the ICP to differentiate into a progenitor/precursor cell population (PCP). Other embodiments are also described.

28 Claims, 8 Drawing Sheets

(56) References Cited

OTHER PUBLICATIONS

Theise N.D., et al. (2000) "Liver From Bone Marrow in Humans" Hepatology 32:11-16.
Kleeberger W. et al.,"High Frequency of Epithelial Chimerism in Liver Transplants Demonstrated by Microdissection and STR-Analysis," Hepatology 35:110-116.
Weimann J.M. et al. (2003), "Contribution of Transplanted Bone Marrow Cells to Purkinje Neurons in Human Adult Brains," Proc. Natl. Acad. Sci. USA 100: 2088-2093.
Blau H.M. et al. (2001),"The Evolving Concept of a Stem Cell : Entity or Function?," Cell 105: 829-841.
Krause D.S. (2002),"Plasticity of Marrow-Derived Stem Cells" Gene Ther. 9:754-758.
Wulf G.G. et al. (2001),"Somatic Stem Cell Plasticity" Exp Hematol. 29: 1361-1370.
Pittenger M.F. et al. (1999),"Multilineage Potential of Adult Human Mesenchymal Stem Cells" Science 284:143-147.
Liechty K.W. et al. (2000),"Human Mesenchymal Stem Cells Engraft and Demonstrate Site-Specific Differentiation After in Utero Transplantation in Sheep," Nature Med. 6:1282-1286 XIII.
Jang YY et al.,"Hematopoietic Stem Cells Convert Into Liver Cells Within Days Without Fusion," Nat Cell Biol. 6(6):532-539. Epub May 9, 2004.
Bittner R.E., et al. (1999),"Recruitment of Bone-Marrow-Derived Cells by Skeletal and Cardiac Muscle in Adult Dystrophic MDX Mice," Anat. Embryol. (Berl) 199:391-396.
Mezey E, et al. (2000),"Turning Blood Into Brain: Cells Bearing Neuronal Antigens Generated In Vivo From Bone Marrow" Science. 290(5497):1779-1782.
Douglas W.L., Dimmeler S. (2004),"Therapeutic Angiogenesis and Vasculogenesis for Ischemic Diseases. Part I: Angiogenic Cytokines" Circulation 109:2487-2491.
Douglas W.L., Dimmeler S. (2004),"Therapeutic Angiogenesis and Vasculogenesis for Ischemic Diseases. Part II: Cell-Based Therapy" Circulation 109:2693-2697.
Amit M. et al.,"Clonally Derived Human Emryonic Stem Cell Lines Maintain Pluripotency and Proliferative Potential for Prolonged Periods of Culture," Dev Biol. 227(2):271-278.
Aoki S, Toda S, Sakemi T, Sugihara H (2003),"Culture of Endothelial Cells and Mature Adipocytes Actively Promotes Immature Preadipocyte Development In Vitro," Cell Struct Funct. 28(1):55-60.
Badorff C, et al.,"Transdifferentiation of Blood-Derived Human Adult Endothelial Progenitor Cells Into Functionally Active Cardiomyocytes," Circulation 107(7):1024-1032.
Bianco, P. and Robey P.G. (2001),"Stem Cells in Tissue Engineering" Nature 414:118-121.
Lagasse E, et al. (2001), "Toward Regenerative Medicine," Immunity 14:425-436.
Stock U.A., Vacanti J.P. (2001), "Tissue Engineering: Current State and Prospects," Ann. Rev. Med 52:443-451.
Kim W.S. et al. (1994), "Bone Defect Repair With Tissue-Engineered Cartilage," Plast. Recontr. Surg. 94:580-584.
Petite H. et al. (2000), "Tissue-Engineered Bone Regeneration" Nature Biotechnol. 18:959-963.
Ramiya V.K. et al. (2000), "Reversal of Insulin-Dependent Diabetes Using Islets Generated In Vitro From Pancreatic Stem Cells," Nature Medicine 6:278-282.
Raffi S., Lyden D.(2003), "Therapeutic Stem and Progenitor Cell Transplantation for Organ Vascularization and Regeneration," Nature Medicine 9:702-712.
Gussoni E., Soneoka Y., Strickland C., Buzney E., Khan M., Flint A., Kunkel L., and Mulligan R. (1999),"Dystrophin Expression in the Mdx Mouse Restored by Stem Cell Transplantation," Nature 401 390-394.
Zhao Y. et al. (2003) "A Human Peripheral Blood Monocyte-Derived Subset Acts As Pluripotent Stem Cells," Proc. Natl. Acad. Sci. USA 100:2426-2431.
Kayisli U.A., et al., "Regulation of Angiogenic Activity of Human Endometrial Endothelial Cells in Culture by Ovarian Steroids", J Clin Endocrinol Metab 89:5794-5802.
Dimmeler S. (2005), "Circulating Endothelial Precursors: Identification of Functional Subpopulations," Blood 106(7):2231-2232.
Urbich C. et al. (2004), "Endothelial Progenitor Cells: Characterization and Role in Vascular Biology," Circulation Research 95:343-353.
Quaini F. et al. (2002), "Chimerism of the Transplanted Heart," N. Engl. Med 346:5-15.
Goodell M.A. et al. (2001), "Stem Cell Plasticity in Muscle and Bone Marrow," Ann. NY Acad. Sci. 938:208-220—an abstract.
Rodda SJ, Kavanagh SJ, Rathjen J, Rathjen PD (2002), "Embryonic Stem Cell Differentiation and the Analysis of Mammalian Development," Int J Dev Biol. 46(4):449-458—an abstract.
Wan H., An Y., Zhang Y, Wang Z (2003), "Differentiation of Rat Embryonic Neural Stem Cells Promoted by Co-Cultured Schwann Cells," Chin Med J (Engl). 116(3):428-431 39.
Kollet O, Shivtel S, Chen YQ. et al. (2003), "HGF, SDF-1, and MMP-9 are Involved in Stress-Induced Human CD34+ Stem Cell Recruitment to the Liver" J Clin Invest. 112(2):160-169—an abstract.
Jackson KA, Majka SM, Wang H, Pocius J, Hartley CJ, Majesky MW, Entman ML, Michael LH, Hirschi KK, Goodell MA (2001). "Regeneration of Ischemic Cardiac Muscle and Vascular Endothelium by Adult Stem Cells," J Clin Invest. 107(11) 1395-1402.
Kohji N, Masayuki Y, Yasutaka H. et al. (2004)."Corneal Reconstruction With Tissue-Engineered Cell Sheets Composed of Autologous Oral Mucosal Epithelium," N Engl J Med 351:1187-1196.
Wagers Amy J. et al, "Little Evidence for Developmental Plasticity of Adult Hematopoietic Stem Cells", Science (Washington DC), vol. 297, No. 5590, Sep. 2002.
Shim WSN et al., "Ex Vivo Differentiation of Human Adult Bone Marrow Stem Cells Into Cardiomyocyte-Like Cells", Biochemical and Biophysical Research Communications, Academic Press Inc. Orlando, FL, US, vol. 324, No. 2, Nov. 2004, pp. 481-488.
Yeh ETH al., "Transdifferentiation of Human Peripheral Blood CD34<+>-Enriched Cell Population Into Cardiomyocytes, Endothelial Cells, and Smooth Muscle Cells In Vivo", Circulation, American heart assoc. Dallas, TX, vol. 108, No. 17, Oct. 2003, pp. 2070-2073.
Gazitt Yair, et al. "Expression of Adhesion Molecules on CD34+ Cells in Peripheral Blood of Non-Hodgkin's Lymphoma Patients Mobilized With Different Growth Factors", Stem Cells (Miamisburg), vol. 19, No. 2, 2001, pp. 134-143.
Murry C et al., "Hematopoietic Stem Cells Do Not Transdifferentiate Into Cardiac Myocytes in Myocardial Infarcts", Nature 20040408nGB, vol. 428, No. 6983, Apr. 2004, pp. 664-448.
Nygren JM et al.,"Bone Marrow-Derived Hematopoietic Cells Generate Cardiomyocytes At a Low Frequency Through Cell Fusion, But Not Transdifferentiation", Nature Medicine May 2004 GB, vol. 10, No. 5 May 2004, pp. 494-501.
European Search Report issued Aug. 4, 2008 in connection with European Patent Application No. 05817711.
European Search Report issued Nov. 18, 2008 in connection with European Patent Application No. 05817711.
European Search Report issued Dec. 21, 2009 in connection with European Patent Application No. 05817711.
Hur, J. et al., (2004) "Characterization of two types of endothelial progenitor cells and their different contributions to neovasculogenesis," *Arteriosclerosis Thrombosis, and Vascular Biology* 24(2): 288-293.
Kocher, A. et al., (2006) "Myocardial homing and neovascularization by human bone marrow angioblasts is regulated by IL-8IGro CXC cheinokines," Abstract only, *Journal of Molecular and Cellular Cardiology* 40(4):455-464.
Anonymous, (2000) "OPTIPREP compared to other density gradient media," *OPTIPREP Reports*, (online) No. 3, http://www.axis-shield.com/densityhome/density/opti_prep.pdf.
Asahara, T. et al., (Feb. 14, 1997) "Isolation of putative progenitor endothelial cells for angiogenesis," *Science*: Washington, D.C., 275(5302):964-967.

(56) References Cited

OTHER PUBLICATIONS

Kubota, Y. et al., (Jan. 1, 2003) "Transplanted endothelial progenitor cells augment the survival areas of rat dorsal flaps," *Cell Transplantation*, Elsevier Science: US, 12(6):647-657.
Metcalf, D. et al., (Jan. 1, 1971) "Adherence column and buoyant density separation of bone marrow stem cells and more differentiated cells," *Journal of Cellular Physiology*, Liss: New York, 78(1):441-450.
International Preliminary Report on Patentability issued by the International Bureau of WIPO dated Jun. 19, 2007 in connection with International Application No. PCT/IL2005/001345.
International Search Report issued by the International Searching Authority (ISA/US) on May 15, 2007 in connection with International Application No. PCT/IL2005/001345.
Written Opinion of the International Searching Authority issued by the International Searching Authority (ISA/US) on May 15, 2007 in connection with International Application No. PCT/IL2005/001345.
An Office Action dated Jun. 4, 2012, which issued during the prosecution of Canadian Patent Application No. 2,632,834.
Aoki M et al., Stem Cells, vol. 22, pp. 994-1002, 2004.
Graham J.M. et al., Peer Reviewed Protocol, vol. 2, pp. 1540-1543, 2002.
Porat, U.S. Appl. No. 60/668,739, published Jun. 22, 2006.
Porat et al., U.S. Appl. No. 60/636,391, published Jun. 22, 2006.
Examination Report issued Oct. 8, 2010 in connection with European Patent Application No. 05 817 711.4.
An Examination Report dated Dec. 2, 2011, which issued during the prosecution of Applicant's European App No. 07713328.
Hur J. et al. "Characterization of two types of Endothelial progenitor cells and their different contribution to neovasculargenesis", Hypertension, 2004; 24:1-6.
A Restriction Requirement dated May 4, 2011, which issued during the prosecution of Applicant's U.S. Appl. No. 11/628,488.
Martin, et al., "Gradient separation of granulocytic progenitor cells (CFUc) from human blood mononuclear leukocytes", Exp. Hematol. 1985, 13:79-86.
An Office Action dated Jun. 16, 2011, which issued during the prosecution of Applicant's Singapore Patent Application No. 200806543-5.
U.S. Appl. No. 60/668,739, filed Apr. 5, 2005, published Jun. 22, 2006.
U.S. Appl. No. 60/636,391, filed Dec. 14, 2004, published Jun. 22, 2006.
An Office Action dated Sep. 26, 2013, which issued during the prosecution of European Patent Application No. 07 713 328.8.
De Almeida M C et al:"A simple method for Human Peripheral Blood Monocyte Isolation", Memorias Do Instirudo Oswaldo Cruz, Rio De Janeiro, BR, vol. 95, No. 2,Jan. 1, 2000, pp. 221-223, XP003023526.
An Office Action dated Nov. 4, 2013, which issued during the prosecution of Canadian Patent Application No. 2,632,836.
An Office Action dated Jul. 26, 2013, which issued during the prosecution of European Patent Application No. 10190450.6.
Oritz-Gonzales Xilma R et al:"Neural induction of adult bone marrow and umbilical cord stem cells"., Current Neurovascular Research Jul. 2004, vol. 1, No. 3, Jul. 2004, pp. 207-213, XP001538190, ISSN: 1567-2026.
An International Preliminary Report on Patentability dated Mar. 10, 2009, which issued during the prosecution of Applicant's PCT/IL2007/000308.
An Office Action dated Jul. 31, 2013, which issued during the prosecution of Canadian Patent Application No. 2,645,142.
Dooley et al, International Journal of Cell Cloning, 6, pp. 45-49, 1988.
Graziani-Bowering et al, Journal of Immunological Methods, 207, pp. 157-168, 1997.
Kalka et al, Proceedings of the National Academy of Sciences, 97(7), pp. 3422-3427, 2000.
An Office Action dated Apr. 19, 2013, which issued during the prosecution of Canadian Patent Application No. 2,632,834.
An Office Action dated Feb. 21, 2013, which issued during the prosecution of Canadian Patent Application No. 2,567,578.
Castro et al., Failure of Bone Marrow Cells to Transdifferentiate into Neural Cells in Vivo, XP-002487072,Science vol. 297, p. 1299, 2002.
Price et al., Multipotent Adult Progenitor Cell Lines Originating from the Peripheral Blood of Green Fluorescent Protein Transgenic Swine, Stem Cells and Development 15:507-522, 2006.
Kim et al., Neural differentiation potential of peripheral blood- and bone-marrow-derived precursor cells BrainResearc H1123, pp. 27-33, 2006. Dec. 15, 2114.
An Office Action dated Feb. 19, 2014, which issued during the prosecution of Canadian Patent Application No. 2,567,578.
An Office Action dated Dec. 19, 2013, which issued during the prosecution of U.S. Appl. No. 11/820,991.
Canadian Office Action issued on Oct. 18, 2012 in CA Application No. 2,632,836.
Office Action issued on Nov. 6, 2012 in U.S. Appl. No. 12/224,913.
Bagley, et al, "Endothelial Precursor Cells As a Model of Turmor", Cancer Research, vol. 63, pp. 5866-5873, 2003.
Bompais, et al, "Human endothelial cells derived from circulating progenitors display specific functional properties compared with mature vessel wall endothelial cells", Blood, vol. 103, pp. 2577-2584, 2004.
Finkenzeller, et al, "Impaired in vivo vasculogenic potential of endothelial progenitor cells in comparison to human umbilical vein endothelial cells in a spheroid-based implantation model", Cell Proliferation, vol. 42, pp. 498-505, 2009.
Hu, et al, "An agiogenin-binding protein from endothelial cells", Biochemistry, vol. 88, pp. 2227-2231, 1991.
Ingram, et al, "Vessel wall-derived endothelial cells rapidly proliferate because they contain a complete hierarchy of endothelial progenitor cells", vol. 105, pp. 2783-2786, 2005.
Canadian Office Action issued Mar. 31, 2014 in CA application No. 2,632,834.
An Office Action dated Jul. 23, 2014 which issued during the prosecution of U.S. Appl. No. 11/820,991.

\* cited by examiner

REGULATING STEM CELLS

BACKGROUND OF THE INVENTION

Since the discovery of stem cells, it has been understood that they have significant potential to effectively treat many diseases [1]. Pluripotent embryonic stem cells derived from embryos and fetal tissue have the potential to produce more than 200 different known cell types, and thus can potentially replace dying or damaged cells of any specific tissue [2, 3]. Stem cells differ from other types of cells in the body, and, regardless of their source, have three general properties: (a) they are capable of dividing and renewing themselves for long periods, (b) they are undifferentiated, and (c) they can give rise to specialized cell types.

Stem cells have been identified in most organs and tissues, and can be found in adult animals and humans. Committed adult stem cells (also referred as somatic stem cells) were identified long ago in bone marrow. In the past decade committed adult stem cells have also been identified in tissues that were previously not thought to contain them, such as brain tissue, skin tissue, and skeletal muscle tissue [8, 9, 10, 11, 12, 13]. It was initially believed that adult stem cells are tissue-committed cells that can only differentiate into cells of the same tissue and thus regenerate the damaged tissue [1, 4, 5, 6, 7]. However, recent work suggests that adult organ-specific stem cells are capable of differentiating into cells of different tissues [8, 9, 10, 11, 14, 16]. Transplantation of cells derived from brain, muscle, skin and fat tissue has been shown to result in a detectable contribution in several lineages distinct from their tissue of origin [8, 9, 10, 11]. For example, recent reports support the view that cells derived from hematopoietic stem cells (HSCs) can differentiate into cells native to the adult brain [14], providing additional evidence for the plasticity of such stem cells.

The HSC is the best characterized stem cell. This cell, which originates in bone marrow, peripheral blood, cord blood, the fetal liver, and the yolk sac, generates blood cells and gives rise to multiple hematopoietic lineages. As early as 1998 researchers reported that pluripotent stem cells from bone marrow can, under certain conditions, develop into several cell types different from known hematopoietic cells [13, 17, 18, 19, 20, 21, 22, 23, 24, 25, 26, 27]. Such an ability to change lineage is referred to as cellular transdifferentiation or cell plasticity. Bone marrow-derived stem cells (BMSCs) have already been shown to have the ability to differentiate into adipocytes, chondrocytes, osteocytes, hepatocytes, endothelial cells, skeletal muscle cells, and neurons [28, 29, 30, 31, 32].

The process of stem cell differentiation is controlled by internal signals, which are activated by genes within the cell, and by external signals for cell differentiation that include chemicals secreted by other cells, physical contact with neighboring cells, and certain molecules in the microenvironment [33, 34]. For example, if embryonic stem cells are allowed to clump together to form embryoid bodies, they begin to differentiate spontaneously. They can form muscle cells, nerve cells, and many other cell types [35, 36]. Although spontaneous differentiation is a good indication that a culture of embryonic stem cells is healthy, it is not an efficient way to produce cultures of specific cell types. In order to generate cultures of specific types of differentiated cells—heart muscle cells, blood cells, or nerve cells, for example—scientists must control the multiplication and the differentiation of stem cells by modifying the chemical composition of the culture medium, altering the surface of the culture dish, or by inserting specific genes.

Successful attempts have been made in vitro to induce differentiation of adult stem cells into other cells by co-culturing with other adult cells. For example, recent work has shown that co-culturing adult mouse BMSCs and embryonic heart tissue causes the BMSCs to both integrate into cardiac tissue and differentiate into cardiomyocytes (CMCs). Other work has shown that mesenchymal stem cells acquire characteristics of cells in the periodontal ligament when co-cultured with periodontal ligament tissue [37, 38].

Tissue injury may be one of the stimulants for the recruitment of stem cells to an injured site, by causing changes in the tissue environment, thereby drawing stem cells from peripheral blood, as well as triggering tissue replacement by locally resident stem cells. Reports of elevated levels of chemokines and chemokine receptors such as CXCR4-SDF explain some of this in vivo stem cell recruitment [39]. An example of this mechanism can be seen in recent work showing that stem cells become liver cells when co-cultured with injured liver cells separated from the stem cells by a barrier [30].

Regenerative medicine is an emerging scientific field with implications for both basic and practical research. Stem and progenitor cells are applied in a form of cellular therapy for local tissue repair and regeneration [41, 42]. These treatments aim to treat disorders in practically all tissues and organs, such as the bladder, intestine, kidney, trachea, eye, heart valves, and bones [43, 44]. Intensive studies are being conducted worldwide in order to generate stem cell-based tissue engineering therapies. These studies include experiments for the regeneration of blood vessels [13], bone [35, 45], cartilage, cornea, dentin, heart muscle [46], liver, pancreas [47], nervous tissue, skeletal muscle, and skin [18, 34, 48, 49]. Stem cell-based therapies can use cells from various organs in order to generate different tissues. For example, epithelial surfaces (taken from various tissues such as the skin, cornea and mucosal membrane) may be used as a source for corneal and skeletal tissues [50, 51]. Additionally, in a more widespread application, blood marrow-derived stem cells are used for regeneration of several different tissues such as bone, cartilage, adipocytes, neurons, and cells of the hematopoietic system [33, 42].

The following references, which are incorporated herein by reference, may be of interest:
1. Leblond C. P. (1964), "Classification of cell populations on the basis of their proliferative behaviour," Natl. Cancer Inst. Monogr. 14:119-150
2. Evans M. J. and Kaufman M. H. (1981), "Establishment in culture of pluripotential cells from mouse embryos," Nature 292:154-156
3. Donovan P. J. and Gearhart J. (2001), "The end of the beginning for pluripotent stem cells," Nature 414:92-97
4. Spradling A. et al. (2001), "Stem cells find their niche," Nature 414:98-104
5. Weissman I. L. et al. (2001), "Stem and progenitor cells: origins, phenotypes, lineage commitments, and transdifferentiations," Annu. Rev. Cell. Dev. Biol. 17:387-403
6. Weissman I. L. (2000), "Stem cells: units of development, units of regeneration, and units in evolution," Cell 100: 157-68
7. Cheng A, Wang S, Cai J, Rao M S, Mattson M P (2003), "Nitric oxide acts in a positive feedback loop with BDNF to regulate neural progenitor cell proliferation and differentiation in the mammalian brain," Dev Biol. 258(2):319-33
8. Cousin B, Andre M, Arnaud E, Penicaud L, Casteilla L (2003), "Reconstitution of lethally irradiated mice by cells isolated from adipose tissue," Biochem Biophys Res Commun. 301(4):1016-22

9. Anderson D. J., Gage, F. H., and Weissman, I. L. (2001), "Can stem cells cross lineage boundaries?" Nat. Med. 7:393-395
10. Robey P. G. (2000), "Stem cells near the century mark," J. Clin. Invest. 105:1489-1491
11. Eisenberg L M, Burns L, Eisenberg C A (2003), "Hematopoietic cells from bone marrow have the potential to differentiate into cardiomyocytes in vitro," Anat Rec. 274A (1):870-82
12. Karl J. L., Fernandes Ian A. McKenzie, Pleasantine Mill et al. (2004), "A dermal niche for multipotent adult skin-derived precursor cells," Nature Cell Biology Published online: 1 Nov. 2004, DOI: 10.1038/ncb1181
13. Jackson K A, Mi T, Goodell M A (1999), "Hematopoietic potential of stem cells isolated from murine skeletal muscle," Proc Natl Acad Sci USA 96(25):14482-6
14. Brazelton T R, Rossi F M, Keshet G I, Blau H M (2000), "From marrow to brain: expression of neuronal phenotypes in adult mice," Science 290(5497):1775-9
15. Bjornson C R, Rietze R L, Reynolds B A, Magli M C, Vescovi A L (1999), "Turning brain into blood: a hematopoietic fate adopted by adult neural stem cells in vivo," Science 283(5401):534-7
16. Slack, J. M. (2000), "Stem cells in epithelial tissues," Science 287:1431-1433
17. Ferrari G., Cusella-De Angelis G., Coletta M., Paolucci E., Stornaiuolo A., Cossu G., and Mavilio F. (1998), "Muscle regeneration by bone marrow-derived myogenic progenitors," Science 279:528-30
18. Lagasse E, Connors H, Al-Dhalimy M, Reitsma M, Dohse M, Osborne L, Wang X, Finegold M, Weissman I L, Grompe M (2000), "Purified hematopoietic stem cells can differentiate into hepatocytes in vivo," Nat Med. 6:1229-34
19. Hirschi, K. K., and Goodell, M. A. (2002), "Hematopoietic, vascular and cardiac fates of bone marrow-derived stem cells," Gene Ther. 9:648-652
20. Theise N. D. et al. (2000), "Liver from bone marrow in humans," Hepatology 32:11-16
21. Kleeberger W. et al. (2002), "High frequency of epithelial chimerism in liver transplants demonstrated by microdissection and STR-analysis," Hepatology 35:110-116
22. Weimann J. M. et al. (2003), "Contribution of transplanted bone marrow cells to Purkinje neurons in human adult brains," Proc. Natl. Acad. Sci. USA 100:2088-2093
23. Quaini F. et al. (2002), "Chimerism of the transplanted heart," N. Engl. Med 346:5-15
24. Blau H. M. et al. (2001), "The evolving concept of a stem cell: entity or function?" Cell 105:829-841
25. Goodell M. A. et al. (2001), "Stem cell plasticity in muscle and bone marrow," Ann. NY Acad. Sci. 938:208-218
26. Krause D. S. (2002), "Plasticity of marrow-derived stem cells," Gene Ther. 9:754-758
27. Wulf G. G. et al. (2001), "Somatic stem cell plasticity," Exp Hematol. 29:1361-1370
28. Pittenger M. F. et al. (1999), "Multilineage potential of adult human mesenchymal stem cells," Science 284:143-147
29. Liechty K. W. et al. (2000), "Human mesenchymal stem cells engraft and demonstrate site-specific differentiation after in utero transplantation in sheep," Nature Med. 6:1282-1286
30. Jang Y Y, Collector M I, Baylin S B, Diehl A M, Sharkis S J (2004), "Hematopoietic stem cells convert into liver cells within days without fusion," Nat Cell Biol. 6(6):532-9. Epub 2004 May 9
31. Bittner R. E., Schofer C., Weipoltshammer K., Ivanova S., Streubel B., Hauser E., Freilinger M., Hoger H., Elbe-Burger A., and Wachtler F. (1999), "Recruitment of bone-marrow-derived cells by skeletal and cardiac muscle in adult dystrophic mdx mice," Anat. Embryol. (Berl) 199: 391-396
32. Mezey E, Chandross K J, Harta G, Maki R A, McKercher S R (2000), "Turning blood into brain: cells bearing neuronal antigens generated in vivo from bone marrow," Science. 290(5497):1779-82
33. Douglas W. L., Dimmeler S. (2004), "Therapeutic angiogenesis and vasculogenesis for ischemic diseases. Part I: Angiogenic cytokines," Circulation 109:2487-2491
34. Douglas W. L., Dimmeler S. (2004), "Therapeutic angiogenesis and vasculogenesis for ischemic diseases. Part II: Cell-based therapy," Circulation 109:2692-2697
35. Rodda S J, Kavanagh S J, Rathjen J, Rathjen P D (2002), "Embryonic stem cell differentiation and the analysis of mammalian development," Int J Dev Biol. 46(4):449-58
36. Amit M., Carpenter M. K., Inokuma M. S., Chiu C. P., Harris C. P., Waknitz M. A., Itskovitz-Eldor J., and Thomson J. A. (2000), "Clonally derived human embryonic stem cell lines maintain pluripotency and proliferative potential for prolonged periods of culture," Dev Biol. 227(2):271-8
37. Aoki S, Toda S, Sakemi T, Sugihara H (2003), "Coculture of endothelial cells and mature adipocytes actively promotes immature preadipocyte development in vitro," Cell Struct Funct. 28(1):55-60
38. Wan H, An Y, Zhang Z, Zhang Y, Wang Z (2003), "Differentiation of rat embryonic neural stem cells promoted by co-cultured Schwann cells," Chin Med J (Engl). 116(3): 428-31
39. Kollet O, Shivtiel S, Chen Y Q. et al. (2003), "HGF, SDF-1, and MMP-9 are involved in stress-induced human CD34+ stem cell recruitment to the liver," J Clin Invest. 112(2):160-9
40. Badorff C, Brandes R P, Popp R, Rupp S, Urbich C, Aicher A, Fleming I, Busse R, Zeiher A M, Dimmeler S (2003), "Transdifferentiation of blood-derived human adult endothelial progenitor cells into functionally active cardiomyocytes," Circulation 107(7):1024-32
41. Bianco, P. and Robey P. G. (2001), "Stem cells in tissue engineering," Nature 414:118-121
42. Lagasse E. et al. (2001), "Toward regenerative medicine," Immunity 14:425-436
43. Stock U. A., Vacanti J. P. (2001), "Tissue engineering: current state and prospects," Ann. Rev. Med 52:443-451
44. Kim W. S. et al. (1994), "Bone defect repair with tissue-engineered cartilage," Plast. Recontr. Surg. 94:580-584
45. Petite H. et al. (2000), "Tissue-engineered bone regeneration," Nature Biotechnol. 18:959-963
46. Jackson K A, Majka S M, Wang H, Pocius J, Hartley C J, Majesky M W, Entman M L, Michael L H, Hirschi K K, Goodell M A (2001), "Regeneration of ischemic cardiac muscle and vascular endothelium by adult stem cells," J Clin Invest. 107(11):1395-402
47. Ramiya V. K. et al. (2000), "Reversal of insulin-dependent diabetes using islets generated in vitro from pancreatic stem cells," Nature Medicine 6:278-282
48. Rafii S., Lyden D. (2003), "Therapeutic stem and progenitor cell transplantation for organ vascularization and regeneration," Nature Medicine 9:702-712
49. Gussoni E., Soneoka Y., Strickland C., Buzney E., Khan M., Flint A., Kunkel L., and Mulligan R. (1999), "Dystrophin expression in the mdx mouse restored by stem cell transplantation," Nature 401:390-4

50. Zhao Y et al. (2003), "A human peripheral blood monocyte-derived subset acts as pluripotent stem cells," Proc. Natl. Acad. Sci. USA 100:2426-2431
51. Kohji N, Masayuki Y, Yasutaka H. et al. (2004), "Corneal reconstruction with tissue-engineered cell sheets composed of autologous oral mucosal epithelium," N Engl J Med 351:1187-96
52. Kayisli U. A., Luk J, Guzeloglu-Kayisli O. et al. (2005), "Regulation of angiogenic activity of human endometrial endothelial cells in culture by ovarian steroids," J Clin Endocrinol Metab 89:5794-5802
53. Dimmeler S. (2005), "Circulating endothelial precursors: Identification of functional subpopulations," Blood 106 (7):2231-2232
54. Urbich C. et al. (2004), "Endothelial progenitor cells: Characterization and role in vascular biology," Circulation Research 95:343-353

U.S. Pat. No. 6,810,286 to Donovan et al., which is incorporated herein by reference, describes a stimulatory device for the controlled production of angiogenic growth factors. More specifically, a subthreshold pulse generator is used for the local production of vascular endothelial growth factor.

SUMMARY OF THE INVENTION

In the context of the present patent application and in the claims, a "core cell population" (CCP) is a population of at least 5 million cells which have a density of less than 1.072 g/ml, and at least 1% of which are CD34+CD45−/dim. (That is, at least 50,000 of the cells are both (a) CD34 positive and (b) CD45 negative or CD45 dim.)

A CCP is typically, but not necessarily, generated from a hematopoietic source.

For most applications, at least 60% of the CCP is CD31+. (That is, at least 3 million cells out of the 5 million cells are CD31+.)

In accordance with an embodiment of the present invention, a method for producing a progenitor/precursor cell population (PCP) is provided, comprising (a) processing cells extracted from a cell donor to yield a CCP, and (b) stimulating the CCP to differentiate into the progenitor/precursor cell population. In the context of the present patent application and in the claims, "progenitor/precursor" cells are partially differentiated cells that are able to divide and give rise to differentiated cells.

While for some applications described herein the density of the cells in the CCP is less than 1.072 g/ml (as described), for some applications, the CCP has at least 5 million cells having a density of less than 1.062 g/ml.

In the context of the present patent application and in the claims, an "elemental cell population" (ECP) is a population of at least 5 million cells which have a density of less than 1.072 g/ml, at least 1.0% of which are CD34+CD45−/dim, and at least 30% of which are CD14+.

Typically, but not necessarily, at least 40% of the cells in the ECP are CD14+. Typically, but not necessarily, at least 1.5% or at least 2% of the cells in the ECP are CD34+CD45−/dim. For some applications, the ECP has at least 5 million cells having a density of less than 1.062 g/ml. It is typically but not necessarily the case that a CCP is also an ECP. It is noted that although for simplicity embodiments of the present invention are described herein with respect to procedures relating to a CCP, the scope of the present invention includes, in each instance, performing the same procedure in relation to an ECP.

An "initiating cell population" (ICP), in the context of the present patent application and in the claims, is a cell population that can differentiate into a PCP. CCPs and ECPs are both examples of an ICP. An ICP is typically, but not necessarily, created by a process that comprises separating lower density cells (that are included in the ICP) from higher density cells. Such a separation may be accomplished, for example, by use of one or more gradients.

For some applications, the CCP-derived progenitor cells are used as a therapeutic cell product (e.g., for cancer therapy, for tissue regeneration, for tissue engineering, and/or for tissue replacement), as a research tool (e.g., for research of signal transduction, or for screening of growth factors), and/or as a diagnostic tool. When the CCP-derived progenitor cells are used as a therapeutic cell product, they are typically administered to a patient, in whom the progenitor cells mature into the desired end cells themselves (e.g., endothelial cells, retinal cells, etc.).

In an embodiment, a result of a stage in a process described herein is used as a diagnostic indicator. For example, pathology of a patient may be indicated if an in vitro procedure performed on extracted blood of the patient does not produce a CCP, when the same procedure would produce a CCP from cells extracted from a healthy volunteer. Alternatively or additionally, a pathology of a patient may be indicated if an in vitro stimulation procedure performed on an autologous CCP does not produce a desired number of a particular class of progenitor cells, when the same procedure would produce the desired number of a particular class of progenitor cells from a CCP derived from cells of a healthy volunteer. Alternatively or additionally, a pathology of a patient may be indicated if one or more in vitro protocols used to assess a PCP do not yield the same results as a PCP originated from a healthy volunteer. Alternatively or additionally, a pathology of a patient may be indicated if one or more protocols used to assess a PCP following implantation in a patient do not perform as expected (e.g., like a PCP implanted in a healthy animal or human volunteer, or in an animal model of a similar disease).

When hematopoietic stem cells are used as source cells to create the CCP, the resultant CCP is typically, but not necessarily, characterized in that at least 40% of the cells in the CCP are CD14+, and at least 2.2% or at least 2.5% of the cells are CD34+CD45−/dim.

Typically, but not necessarily, the process of stimulating the CCP takes between about 2 and about 15 days (e.g., between about 3 and about 15 days), or between about 15 and about 120 days (e.g., between about 15 and about 30 days). Alternatively, stimulating the CCP takes less than 2 days, or more than 120 days.

The mammalian cell donor may be human or non-human, as appropriate. For some applications, the mammalian cell donor ultimately receives an administration of a product derived from the CCP, while for other applications, the mammalian cell donor does not receive such a product. Stem cells that can be used to produce the CCP may be derived, for example, from one or more of the following source tissues: embryonic tissue, umbilical cord blood or tissue, neonatal tissue, adult tissue, bone marrow, mobilized blood, peripheral blood, peripheral blood mononuclear cells, skin cells, and other stem-cell-containing tissue. It is noted that the stem cells may typically be obtained from fresh samples of these sources or from frozen and then thawed cells from these source tissues.

The CCP is typically prepared by generating or obtaining a single cell suspension from one of these source tissues. For example, mobilized blood mononuclear cells may be extracted using a 1.077 g/ml density gradient (e.g., a Ficoll™ gradient, including copolymers of sucrose and epichlorohydrin). (It is noted that such a gradient is not used for all applications, e.g., for applications in which a single cell suspension is generated from a non-hematopoietic source such as mucosal or skin cells.) The output of this gradient is then typically passed through a second gradient (e.g., a Percoll™ gradient, including polyvinylpyrrolidone-coated silica colloids), suitable for selecting cells having a density less than 1.072 g/ml or less than 1.062 g/ml. These selected cells are then typically increased in number, in vitro, until they become a CCP. As appropriate, other density gradients may be used, in addition to or instead of those cited above. For example, an OptiPrep™ gradient, including an aqueous solution of Iodixanol, and/or a Nycodenz™ gradient may also be used.

The CCP is typically stimulated to generate progenitor cells of one or more of the following cell classes:

Blood cells (e.g., red blood cells and/or white blood cells (such as T cells or B cells));

Neural lineage cells (e.g., CNS neurons, oligodendrocytes, astrocytes, peripheral nervous system (PNS) neurons, and retinal cells (including, but not limited to, photoreceptors, pigment epithelium cells or retinal ganglion cells).

Endothelial cells;
Pericytes;
Smooth muscle cells;
Cardiomyocytes;
Osteoblasts;
Pancreatic endocrine or exocrine cells (e.g., beta cells or alpha cells);
Hepatic tissue (e.g., hepatocytes); and
Kidney cells.

For some applications, the CCP is transfected with a gene prior to the stimulation of the CCP, whereupon the CCP differentiates into a population of desired progenitor cells containing the transfected gene. Typically, these progenitor cells are then administered to a patient. For some applications, the PCP is transfected with a gene. Typically, these PCP cells are then administered to a patient.

To stimulate the CCP to differentiate into a desired class of progenitor cells, or in association with stimulation of the CCP to differentiate into a desired class of progenitor cells, the CCP is typically directly or indirectly co-cultured with "target tissue" (possibly, but not necessarily, a tissue from an organ representing a desired final state of the progenitor cells). For example, the target tissue may include brain or similar tissue, or heart or similar tissue, if it is desired for the progenitor cells to differentiate into brain tissue or into heart tissue. Other examples include:

(a) co-culturing the CCP with peripheral nerves (and/or culturing the CCP in conditioned medium derived therefrom), to induce differentiation of the CCP into peripheral neurons;

(b) co-culturing the CCP with central nervous system (CNS) nerves (and/or culturing the CCP in conditioned medium derived therefrom), to induce differentiation of the CCP into CNS neurons;

(c) co-culturing the CCP with retinal tissue (and/or culturing the CCP in conditioned medium derived therefrom), to induce differentiation of the CCP into retinal tissue. The retinal tissue may include, for example, one or more of: pigment epithelium, or photoreceptors. As appropriate, the retinal tissue may comprise fetal retinal tissue, embryonic retinal tissue, or mature retinal tissue;

(d) co-culturing the CCP with blood vessel tissue (and/or culturing the CCP in conditioned medium derived therefrom), to induce differentiation of the CCP into angiogenic lineage tissue and/or cardiomyocytes (CMCs);

(e) co-culturing the CCP with cardiac tissue (and/or culturing the CCP in conditioned medium derived therefrom), to induce differentiation of the CCP into CMCs;

(f) co-culturing the CCP with pancreatic endocrine or exocrine tissue (and/or culturing the CCP in conditioned medium derived therefrom), to induce differentiation of the CCP into pancreatic endocrine or exocrine cells; and (g) co-culturing the CCP with smooth muscle tissue (and/or culturing the CCP in conditioned medium derived therefrom), to induce differentiation of the CCP into smooth muscle cells.

Techniques described herein with respect to use of a target tissue may be used with any "sample" tissue, regardless of whether it is desired for the CCP to differentiate into a PCP having cells like those in the sample tissue.

For some applications, slices or a homogenate of the target tissue are used for co-culturing, although other techniques for preparing the target tissue will be apparent to a person of ordinary skill in the art who has read the disclosure of the present patent application.

The target tissue may be in essentially direct contact with the CCP, or separated therefrom by a semi-permeable membrane. As appropriate, the target tissue may be autologous, syngeneic, allogeneic, or xenogeneic with respect to the source tissue from which the CCP was produced. Alternatively or additionally, the CCP is cultured in a conditioned medium made using target tissue (e.g., a target tissue described hereinabove), that is autologous, syngeneic, allogeneic, or xenogeneic with respect to the source tissue from which the CCP was produced. For some applications, the target tissue and the CCP are cultured together in the conditioned medium. It is noted that the source of the target tissue may also be tissue from a cadaver, and/or may be lyophilized, fresh, or frozen.

Alternatively or additionally, for some applications, to produce a desired class of progenitor cells, cells from the CCP are cultured in the presence of stimulation caused by "stimulation factors," e.g., one or more antibodies, cytokines, growth factors, tissue-derived extra cellular matrix, and/or other molecules, such as: anti-CD34, anti-Tie-2, anti-CD133, anti-CD117, LIF, EPO, IGF, b-FGF, M-CSF, GM-CSF, TGF alpha, TGF beta, VEGF, BHA, BDNF, NGF, NT3, NT4/5, GDNF, S-100, CNTF, EGF, NGF3, CFN, ADMIF, estrogen, cortisone, dexamethasone, or any other molecule from the steroid family, prolactin, an adrenocorticoid, glutamate, serotonin, acetylcholine, NO, retinoic acid (RA), heparin, insulin, forskolin, a statin, or an anti-diabetic drug (e.g., a thiazolidinedione such as rosiglitazone), NO, MCDB-201, sodium selenite, linoleic acid, ascorbic acid, transferrin, 5-azacytidine, PDGF, VEGF, cardiotrophin, and thrombin.

It is to be appreciated that the particular stimulation factors described herein are by way of illustration and not limitation, and the scope of the present invention includes the use of other stimulation factors. As appropriate, these may be utilized in a concentration of between about 100 pg/ml and about 100 μg/ml (or molar equivalents). Typically, particular stimulation factors are selected in accordance with the particular class of progenitor cells desired. For example, to induce neuronal progenitor cells, one or more of the following stimulation factors are used: BHA, BDNF, NGF, NT3, NT4/5, GDNF, S-100, CNTF, EGF, NGF3, CFN, ADMIF, and acetylcholine. In another example, to induce CMC progenitors, one or more of the following stimulation factors are used: bFGF, cortisone, estrogen, progesterone, or any other molecule form the steroid family, NO, sodium selenite, linoleic acid, ascorbic acid, retinoic acid (RA), transferrin, 5-azacytidine, TGF-beta, insulin, EGF, IGF, PDGF, VEGF, cardiotrophin, MCDB201, and thrombin).

For some applications, the stimulation factors are introduced to the CCP in a soluble form, and/or in an aggregated form, and/or attached to a surface of a culture dish. In an embodiment, the CCP is incubated on a surface comprising a growth-enhancing molecule other than collagen or fibronectin. The growth-enhancing molecule may comprise, for example, VEGF or another suitable antibody or factor described herein. As appropriate, the growth-enhancing molecule may be mixed with collagen or fibronectin or plasma, or may be coated on the surface in a layer separate from a layer on the surface that comprises collagen or fibronectin or plasma. Alternatively, the only growth-enhancing molecule(s) on the surface is collagen and/or fibronectin and/or plasma.

In the context of the present patent application and in the claims, a surface "comprising" or "including" a molecule means that the molecule is coated on the surface, attached to the surface, or otherwise integrated into the surface.

Following stimulation of the CCP, the resultant product is typically tested to verify that it has differentiated into a desired form. Characterization of differentiated cells is performed according to the cells' phenotypical, genotypical and physiological features. In accordance with an embodiment of the present invention, cells are characterized by assessing functional/physiological activity of the cells, in addition to or instead of evaluating the presence or absence of certain cellular markers. The inventors hypothesize that evaluating functional/physiological activity of cells following the stimulation of the CCP increases the likelihood that the product obtained and designated for in vivo use will perform as expected.

For example, when angiogenic cell precursors (ACPs) (which also include endothelial progenitor cells (EPCs)) are the desired product, the product is typically positive for the generation and/or expression of one or more of: CD34, CD117, CD133, Tie-2, CD31, CD34+CD133+, KDR, CD34+KDR+, CD144, von Willebrand Factor, SH2 (CD105), SH3, fibronectin, collagen (types I, III and/or IV), ICAM (type 1 or 2), VCAM1, Vimentin, BMP-R IA, BMP-RII, CD44, integrin b1, aSM-actin, and MUC18, CXCR4. In addition, the ACP product typically functionally demonstrates uptake of Acetylated-Low Density Lipoprotein (Ac-LDL), and/or secretes one or more of the following molecules: Interleukin-8 (IL-8), VEGF, Angiogenin, Matrix metalloproteinase 2 (MMP-2), or Matrix metalloproteinase 9 (MMP-9). Alternatively or additionally, the ACP product generates tube-like structures on a semi-solid matrix, and/or migrates towards chemoattractants (such as SDF-1 or VEGF), and/or proliferates in response to cell activation, and/or generates typical cell colonies/clusters.

Typically, greater than 1.5% of the core cell population that was stimulated demonstrates one or more of these features. Alternatively, if neural progenitor cells are the desired product, then the product is typically positive for the generation and/or the expression of one or more of: Nestin, NSE, Notch, numb, Musashi-1, presenilin, FGFR4, Fz9, SOX 2, CD133, CD15, GD2, rhodopsin, recoverin, calretinin, PAX6, RX, Chx10, O4, and GFAP. If cardiomyocyte (CMC) progenitors are the desired product, then the product is typically positive for the generation and/or the expression of one or more of: CD31, CD117, sarcomeric α-actin, β-actin, α-actinin, desmin, cardiac troponin T, connexin43, α/β-MHC, sarcomeric α-tropomyosin, Troponin I, GATA-4, Nkx2.5/Csx, and MEF-2.

For some applications, an effort is made to minimize the time elapsed from collection of cells from the cell donor until the CCP-derived progenitor cells are used (e.g., for administration into a patient). Alternatively, cells are preserved at one or more points in the process. For example, the CCP may be frozen prior to the stimulation thereof that generates progenitor cells. In another example, the CCP are stimulated in order to generate desired progenitor cells, and these progenitor cells are frozen. In either of these cases, the frozen cells may be stored and/or transported, for subsequent thawing and use.

By way of illustration and not limitation, it is noted that certain applications are suitable for large-scale commercialization, including freezing and transport, such as (a) generation of stores of CCPs, (b) generation of stores of PCPs, (such as hematopoietic stem cells able to mature into CMCs), and (c) stem cell banks where individuals may store a CCP or differentiated progenitor cells, for possible later use. Other applications (such as acute post-stroke autologous administration of neuronal stem cells) may not benefit, or may not benefit as greatly, from the time delays provided by freezing of cells, although the technique may be useful for some purposes. "Transport," in this context, means transport to a remote site, e.g., a site greater than 10 km or 100 km away from a site where the CCP is first created.

For some applications, the CCP is cultured for a period lasting between about 1 and about 20 days (e.g., between about 1 and 5 days) in a culture medium comprising less than about 5% serum. Alternatively, the CCP is cultured for a period lasting between about 1 and about 20 days (e.g., between about 1 and about 5 days) in a culture medium comprising greater than about 10% serum. In an embodiment, one of these periods follows the other of these periods For some applications, the CCP is cultured, during a low-serum time period, in a culture medium comprising less than about 10% serum, and, during a high-serum time period, in a culture medium comprising greater than or equal to about 10% serum. In an embodiment, culturing the CCP during the low-serum time period comprises culturing the CCP for a duration of between about 1 and about 20 days (e.g., between about 1 and about 5 days). Alternatively or additionally, culturing the CCP during the high-serum time period comprises culturing the CCP for a duration of between about 1 and about 120 days (e.g., between about 1 and about 30 days). Typically, culturing the CCP during the low-serum time period is performed prior to culturing the CCP during the high-serum time period. Alternatively, culturing the CCP during the low-serum time period is performed following culturing the CCP during the high-serum time period.

For some applications, during a hypoxic time period lasting at least about 2 hours, the CCP is cultured under hypoxic conditions, and, during a non-hypoxic time period lasting at least about 1 day, the CCP is cultured under non-hypoxic conditions. Culturing the CCP under hypoxic conditions may be performed prior to or following culturing the CCP under non-hypoxic conditions. Typically, but not necessarily, the hypoxic and non-hypoxic time-periods are within a culturing time period lasting less than about 120 days (e.g., less than about 30 days), and culturing the CCP under hypoxic conditions comprises culturing the CCP under hypoxic conditions during the first about two days of the culturing time period. Alternatively or additionally, culturing the CCP under hypoxic conditions comprises culturing the CCP under hypoxic conditions during the last about two days of the culturing time period. Further alternatively or additionally, culturing the CCP under hypoxic conditions comprises culturing the CCP under hypoxic conditions for at least about 2 hours between a first two days and a last two days of the culturing time period.

For some applications, the CCP is cultured in a culture medium comprising at least one of the following: erythropoietin, a statin, and an antidiabetic agent (e.g., a thiazolidinedione such as rosiglitazone). Alternatively or additionally, the CCP is cultured in the presence of one or more proliferation-differentiation-enhancing agents, such as, anti-CD34, anti-Tie-2, anti-CD133, anti-CD117, LIF, EPO, IGF, b-FGF, M-CSF, GM-CSF, TGF alpha, TGF beta, VEGF, BHA, BDNF, NGF, NT3, NT4/5, GDNF, S-100, CNTF, EGF, NGF3, CFN, ADMIF, estrogen, prolactin, an adrenocorticoid, glutamate, serotonin, acetylcholine, NO, retinoic acid (RA), heparin, insulin, forskolin, cortisone, cortisol, dexamethasone, progesterone, or any other molecule from the steroid family, a statin, or an anti-diabetic drug (e.g., a thiazolidinedione such as rosiglitazone), MCDB-201, sodium selenite, linoleic acid, ascorbic acid, transferrin, 5-azacytidine, PDGF, VEGF, cardiotrophin, and thrombin.

In an embodiment, techniques described herein are practiced in combination with (a) techniques described in one or more of the references cited herein, (b) techniques described in U.S. Provisional Patent Application 60/576,266, filed Jun. 1, 2004, and/or (c) techniques described in U.S. Provisional Patent Application 60/588,520, filed Jul. 15, 2004. Both of these provisional patent applications are assigned to the assignee of the present patent application and are incorporated herein by reference.

In an embodiment, a method is provided comprising culturing the CCP in a first container during a first portion of a culturing period; removing all or at least some cells of the CCP from the first container at the end of the first portion of the period; and culturing, in a second container during a second portion of the period, the cells removed from the first container. For example, removing at least some of the CCP cells may comprise selecting for removal cells that adhere to a surface of the first container.

If cells from a progenitor/precursor cell population (PCP) derived from a CCP are to be implanted into a human, they should be generally free from any bacterial or viral contamination. In addition, in the case of a PCP of angiogenic cell precursors (ACPs), one, some, or all of the following phenotypical, genotypical and physiological conditions should typically be met:

(I) Cells should be morphologically characterized as (a) larger in size than 20 µM and/or (b) elongated, spindle-shaped or irregular-shaped and/or (c) granulated or dark nucleated and/or (d) with flagella-like structures or pseudopodia and/or (e) fibroblast-like or polygonal in shape.

(II) Final cell suspension should generally contain at least 1 million cells expressing one or more of the following markers: CD31, CD34, CD117, CD133, Tie-2, CD34+CD133+, KDR, CD34+KDR+, CD144, von Willebrand Factor, SH2 (CD105), SH3, fibronectin, collagen (types I, III and/or IV), ICAM (type 1 or 2), VCAM1, Vimentin, BMP-R IA, BMP-RII, CD44, integrin b1, aSM-actin, and MUC18, CXCR4

(III) Cells should be able to uptake Ac-LDL.

(IV) Cells should generally secrete one or more of the following molecules: IL-8, Angiogenin, VEGF, MMP2, and MMP9.

(V) Cells should generally form tube-like structures when cultured on a semi-solid matrix containing growth factors.

(VI) Cells should generally migrate using chemotaxis towards different chemoattractants, such as SDF-1 and VEGF.

(VII) Cells should generally form typical colonies and/or clusters when cultured in medium supplemented with growth factors such as VEGF and GM-SCF.

It is noted that the cells in CCPs generated from various tissues typically can be characterized as having greater than 75% viability.

It is noted that CCPs generated from blood, bone marrow, and umbilical cord blood, typically have greater than 70% of their cells being CD45+.

In some embodiments of the present invention, a novel composition of matter is provided, comprising (a) a cell population, or (b) a mixture comprising a cell population and molecules produced by the cell population, wherein (a) or (b) are produced by a method described herein (for example, in one of the methods set forth in the following paragraphs preceding the Brief Description section of the present patent application, or in one of the methods described in the Detailed Description section of the present patent application).

There is therefore provided, in accordance with an embodiment of the invention, a method including in vitro stimulating an initiating cell population (ICP) of at least 5 million cells that have a density of less than 1.072 g/ml, and at least 1% of which are CD34+CD45−/dim, to differentiate into a progenitor/precursor cell population (PCP).

There is also provided, in accordance with an embodiment of the invention, a method including in vitro stimulating an initiating cell population (ICP) of at least ten thousand cells that have a density of less than 1.072 g/ml to differentiate into a progenitor/precursor cell population (PCP).

There is further provided, in accordance with an embodiment of the invention, a method including separating lower density cells from higher density cells, the lower density cells defining an initiating cell population (ICP), and in vitro stimulating the ICP to differentiate into a progenitor/precursor cell population (PCP).

In an embodiment, the ICP includes at least 5 million cells, and wherein stimulating the ICP includes stimulating the ICP that includes the at least 5 million cells.

In an embodiment, at least 1.5% of the cells of the ICP are CD34+CD45−/dim, and wherein stimulating the ICP includes stimulating the ICP of which at least 1.5% of the cells are CD34+CD45−/dim.

In an embodiment, at least 2% of the cells of the ICP are CD34+CD45−/dim, and wherein stimulating the ICP includes stimulating the ICP of which at least 2% of the cells are CD34+CD45−/dim.

In an embodiment, at least 30% of the cells of the ICP are CD14+, and wherein stimulating the ICP includes stimulating the ICP of which at least 30% of the cells are CD34+CD45−/dim.

In an embodiment, the ICP includes at least 5 million cells that have a density of less than 1.062 g/ml, at least 1% of which are CD34+CD45−/dim, and wherein stimulating the ICP includes stimulating the ICP that has the at least 5 million cells that have a density of less than 1.062 g/ml.

In an embodiment, at least 60% of cells in the ICP are CD31+, and wherein stimulating the ICP includes stimulating the ICP of which at least 60% of cells therein are CD31+.

In an embodiment, the method includes preparing the PCP as a product for administration to a patient.

In an embodiment, the method includes preparing the PCP as a research tool.

In an embodiment, stimulating the ICP includes only stimulating the ICP if the ICP is derived from a mammalian donor.

In an embodiment, the method includes applying cells extracted from a mammalian donor to one or more gradients suitable for selecting cells having a density less than 1.072 g/ml, and deriving the ICP from the cells applied to the gradient.

In an embodiment, the ICP is characterized by at least 2.5% of the ICP being CD34+CD45−/dim, and wherein stimulating the ICP includes stimulating the ICP having the at least 2.5% of the ICP that are CD34+CD45−/dim.

In an embodiment, the ICP is characterized by at least 50% of the ICP being CD14+, and wherein stimulating the ICP includes stimulating the ICP having the at least 50% of the ICP that are CD14+.

In an embodiment, the ICP is characterized by at least 40% of the ICP being CD14+, and wherein stimulating the ICP includes stimulating the ICP having the at least 40% of the ICP that are CD14+.

In an embodiment, stimulating the ICP includes stimulating the ICP to differentiate into a pre-designated, desired class of progenitor cells.

In an embodiment, the method includes deriving the ICP from at least one source selected from the list consisting of: embryonic tissue, fetal tissue, umbilical cord blood, umbilical cord tissue, neonatal tissue, adult tissue, bone marrow, mobilized blood, peripheral blood, peripheral blood mononuclear cells, skin cells, and plant tissue.

In an embodiment, the method includes deriving the ICP from at least one source selected from the list consisting of: fresh tissue and frozen tissue.

In an embodiment, the method includes identifying an intended recipient of the PCP, and deriving the ICP from at least one source selected from the list consisting of: tissue autologous to tissue of the intended recipient, tissue syngeneic to tissue of the intended recipient, tissue allogeneic to tissue of the intended recipient, and tissue xenogeneic to tissue of the intended recipient.

In an embodiment, stimulating the ICP includes culturing the ICP for a period lasting between 1 and 5 days in a culture medium including less than 5% serum.

In an embodiment, stimulating the ICP includes culturing the ICP for a period lasting between 1 and 5 days in a culture medium including at least 10% serum.

In an embodiment, stimulating the ICP includes culturing the ICP in a culture medium including a factor selected from the list consisting of: erythropoietin, a statin, and an antidiabetic agent.

In an embodiment, stimulating the ICP includes culturing the ICP in a culture medium including a factor selected from the list consisting of: estrogen, prolactin, progestin, an adrenocorticoid, and cortisone.

In an embodiment, stimulating the ICP includes culturing the ICP in a culture medium including a factor selected from the list consisting of: anti-Tie-2, anti-CD133, and anti-CD117.

In an embodiment, stimulating the ICP includes culturing the ICP in the presence of a factor selected from the list consisting of: erythropoietin, a statin, an antidiabetic agent, a thiazolidinedione, rosiglitazone, a proliferation-differentiation-enhancing agent, anti-CD34, anti-Tie-2, anti-CD133, anti-CD117, LIF, EPO, IGF, b-FGF, M-CSF, GM-CSF, TGF alpha, TGF beta, VEGF, BHA, BDNF, GDNF, NGF, NT3, NT4/5, S-100, CNTF, EGF, NGF3, CFN, ADMIF, estrogen, prolactin, an adrenocorticoid, glutamate, serotonin, acetylcholine, NO, retinoic acid (RA), heparin, insulin, and forskolin, cortisone.

In an embodiment, the method includes preparing the ICP, and facilitating a diagnosis responsive to a characteristic of the preparation of the ICP.

In an embodiment, the method includes freezing the ICP prior to stimulating the ICP.

In an embodiment, the method includes freezing the PCP.

In an embodiment, the method includes transporting the ICP to a site at least 10 km from a site where the ICP is first created, and stimulating the ICP at the remote site.

In an embodiment, the method includes transporting the PCP to a site at least 10 km from a site where the PCP is first created.

In an embodiment, the method includes identifying the PCP as being suitable for therapeutic implantation in response to an assessment that the PCP includes at least 1 million PCP cells.

In an embodiment, the method includes identifying the PCP as being suitable for therapeutic implantation in response to an assessment that at least 1.5% of cells of the PCP demonstrate a feature selected from the list consisting of: a desired morphology, a desired cellular marker, a desired cellular component, a desired enzyme, a desired receptor, a desired genotypic feature, and a desired physiological feature.

In an embodiment, the method includes identifying the PCP as being suitable for therapeutic implantation in response to an assessment that the PCP includes at least 1 million angiogenic cell precursors (ACPs).

In an embodiment, the method includes identifying the PCP as being suitable for therapeutic implantation in response to an assessment that the PCP includes at least 1 million cardiomyocyte progenitors.

In an embodiment, the method includes identifying the PCP as being suitable for therapeutic implantation in response to an assessment that the PCP includes at least 1 million neural cell progenitors.

In an embodiment, the method includes transfecting into the PCP a gene identified as suitable for gene therapy.

In an embodiment, the method includes transfecting a gene into the PCP, and subsequently assessing a level of expression of the gene.

In an embodiment, the method includes transfecting a gene into the ICP, and subsequently assessing a level of expression of the gene.

In an embodiment, stimulating the ICP includes culturing the ICP during a period of between 2 and 120 days.

In an embodiment, stimulating the ICP includes culturing the ICP during a period of between 3 and 60 days.

In an embodiment, stimulating the ICP includes culturing the ICP in a culture medium including less than 10% serum, for a duration of between 1 and 120 days.

In an embodiment, stimulating the ICP includes culturing the ICP in a culture medium including at least 10% serum, for a duration of between 1 and 120 days.

In an embodiment, the method includes characterizing the PCP as including angiogenic cell precursors (ACPs), in response to an evaluation of at least a feature selected from the list consisting of: a phenotypical feature of cells in the PCP, a genotypical feature of cells in the PCP, and a physiological feature of cells in the PCP.

In an embodiment, characterizing the PCP includes characterizing the PCP in response to an evaluation of at least two of the features.

In an embodiment, characterizing the PCP includes characterizing the PCP in response to an evaluation of each of the features.

In an embodiment:
the phenotypical feature includes a morphological feature selected from the list consisting of: a cell size larger than 20 µm, an elongated cell, a spindle-shaped cell, an irregularly-shaped cell, a granulated cell, a cell including an enlarged dark nucleus, a multinuclear cell, a cell including flagella-like structures, a cell including pseudopodia, and a cell having a polygonal shape; and characterizing the PCP includes characterizing the PCP in response to an evaluation of the selected morphological feature.

In an embodiment, characterizing the PCP includes identifying that at least 1.5% of cells of the PCP have the selected feature.

In an embodiment, characterizing the PCP includes characterizing the PCP in response to an identification in the PCP of a feature selected from the list consisting of: CD31, CD34, CD117, CD133, Tie-2, CD34+CD133+, KDR, CD34+ KDR+, CD144, von Willebrand Factor, SH2 (CD105), SH3, fibronectin, collagen type I, collagen type III, collagen type IV, ICAM type 1, ICAM type 2, VCAM1, vimentin, BMP-R IA, BMP-RII, CD44, integrin b1, aSM-actin, MUC18, and CXCR4.

In an embodiment, characterizing the PCP includes identifying that at least 1.5% of cells of the PCP have the selected feature.

In an embodiment, characterizing the PCP includes characterizing the PCP in response to an assessment of uptake by the PCP of Ac-LDL.

In an embodiment, characterizing the PCP includes identifying that at least 1.5% of cells of the PCP demonstrate uptake of Ac-LDL.

In an embodiment, characterizing the PCP includes assessing secretion by the PCP of a molecule selected from the list consisting of: IL-8, angiogenin, VEGF, MMP2, and MMP9.

In an embodiment, characterizing the PCP includes identifying that at least 1.5% of cells of the PCP secrete the selected molecule.

In an embodiment, characterizing the PCP includes culturing a portion of the PCP on a semi-solid extracellular matrix (ECM), and identifying in the cultured portion a feature selected from the list consisting of: a tube-like structure, a colony, a cluster, and a tendency to migrate towards a chemoattractant.

In an embodiment, characterizing the PCP includes identifying that at least 1.5% of cells in the cultured portion have a property selected from the list consisting of: formation of a tube-like structure, an ability to form a colony, a cluster, and a tendency to migrate towards a chemoattractant.

In an embodiment, the method includes including identifying the PCP as being suitable for therapeutic implantation in response to an assessment that the PCP includes at least 1 million ACPs.

In an embodiment, the method includes characterizing the PCP as including a cardiomyocyte (CMC) PCP in response to an evaluation of a feature selected from the list consisting of: a phenotypic feature of cells in the PCP, a genotypic feature on the cells in the PCP, and a physiological feature of cells in the PCP.

In an embodiment, characterizing the PCP includes characterizing the PCP in response to an evaluation of at least two of the features.

In an embodiment, the method includes characterizing the PCP includes characterizing the PCP in response to an evaluation of each of the features.

In an embodiment, the phenotypic feature includes a morphological feature selected from the list consisting of: a cell size larger than 20 µm, an elongated cell, an irregularly-shaped cell, a granulated cell, a cell including an enlarged dark nucleus, a multinuclear cell, a cell with dark cytoplasm, and cells arranged in parallel to each other; and wherein characterizing the PCP includes characterizing the PCP in response to an evaluation of the selected morphological feature.

In an embodiment, characterizing the PCP includes characterizing the PCP in response to an identification in the PCP of a feature selected from the list consisting of: CD31, CD117, sarcomeric α-actin, β-actin, α-actinin, desmin, cardiac troponin T, Connexin-43, α/β-MHC, sarcomeric α-tropomyosin, Troponin I, GATA-4, Nkx2.5/Csx, MLC-2, and MEF-2.

In an embodiment, characterizing the PCP includes characterizing the PCP in response to an identification of the PCP as expressing a gene for a factor selected from the list consisting of: sarcomeric α-actin, β-actin, α-actinin, desmin, cardiac troponin T, Connexin-43, α/β-MHC, sarcomeric α-tropomyosin, Troponin I, GATA-4, Nkx2.5/Csx, MLC-2 and MEF-2.

In an embodiment, the method includes identifying the PCP as being suitable for therapeutic implantation in response to an assessment that the PCP includes at least 1 million CMC progenitors.

In an embodiment, characterizing the PCP includes identifying that at least 1.5% of cells of the PCP have a characteristic selected from the list consisting of: a CMC-progenitor morphological characteristic, expression of a CMC-associated cellular marker, expression of a CMC-progenitor gene product, and expression of a CMC-progenitor physiological feature.

In an embodiment, characterizing the PCP includes characterizing the PCP in response to an identification in the PCP of an action in response to activation of the PCP, the action selected from the list consisting of: increasing intracellular $Ca^{2+}$ level, generating membranal electrophysiological action potentials, and mechanical cellular contraction in vitro.

In an embodiment, the method includes activating the PCP to produce the selected action, using a technique selected from the list consisting of: electrical activation of the PCP, and chemical activation of the PCP.

In an embodiment, the method includes:
assessing a phenotypic aspect of the PCP and a genotypic aspect of the PCP and a physiological aspect of the PCP; and
designating the PCP as being suitable for implantation in a patient in response to each of the assessments.

In an embodiment, assessing the phenotypic aspect of the PCP includes assessing an aspect of the PCP selected from the list consisting of: morphology of the PCP, a cellular marker of cells of the PCP, an enzyme of the PCP, a coenzyme of the PCP, and presence of a designated cellular receptor on cells of the PCP.

In an embodiment, assessing the genotypic aspect of the PCP includes assessing an aspect of the PCP selected from the list consisting of: production of a gene by cells of the PCP, expression of a gene by cells of the PCP, and generation of a gene product by cells of the PCP.

In an embodiment, assessing the physiological aspect of the PCP includes assessing an aspect of the PCP selected from the list consisting of: secretion of soluble molecules by cells of the PCP, generation of signals by cells of the PCP, response by cells of the PCP to signals, and an enzymatic reaction performed by cells of the PCP.

In an embodiment, the method includes facilitating a diagnosis responsive to stimulating the ICP to differentiate into the PCP.

In an embodiment, facilitating the diagnosis includes assessing an extent to which the stimulation of the ICP produces a particular characteristic of the PCP.

In an embodiment, the method includes transfecting a gene into the ICP prior to stimulating the ICP.

In an embodiment, transfecting the gene includes transfecting into the ICP a gene identified as suitable for gene therapy.

In an embodiment, the method includes preparing, as a product for administration to a patient, the PCP generated by differentiation of the ICP into which the gene has been transfected.

In an embodiment, the method includes stimulating the ICP includes incubating the ICP in a container having a surface including a growth-enhancing factor.

In an embodiment, the method includes the growth-enhancing factor is selected from the list consisting of: collagen, plasma, fibronectin, a growth factor, tissue-derived extra cellular matrix, and an antibody to a stem cell surface receptor.

In an embodiment, stimulating the ICP includes incubating the ICP in a container with a surface including a growth-enhancing molecule other than collagen or fibronectin.

In an embodiment, incubating the ICP includes incubating the ICP in a container having a surface that includes, in addition to the growth-enhancing molecule, at least one of: collagen and fibronectin.

In an embodiment, the method includes mixing the growth-enhancing molecule with the at least one of: collagen and fibronectin.

In an embodiment, the method includes applying to the surface a layer that includes the growth-enhancing molecule and a separate layer that includes the at least one of: collagen and fibronectin.

In an embodiment, stimulating the ICP includes:
during a low-serum time period, culturing the ICP in a culture medium including less than 10% serum; and
during a high-serum time period, culturing the ICP in a culture medium including greater than or equal to 10% serum.

In an embodiment, culturing the ICP during the low-serum time period includes culturing the ICP for a duration of between 1 and 60 days.

In an embodiment, culturing the ICP during the low-serum time period includes culturing the ICP for a duration of between 1 and 5 days.

In an embodiment, culturing the ICP during the high-serum time period includes culturing the ICP for a duration of between 1 and 120 days.

In an embodiment, culturing the ICP during the high-serum time period includes culturing the ICP for a duration of between 1 and 60 days.

In an embodiment, culturing the ICP during the low-serum time period is performed prior to culturing the ICP during the high-serum time period.

In an embodiment, culturing the ICP during the low-serum time period is performed following culturing the ICP during the high-serum time period.

In an embodiment, the method includes:
during a hypoxic time period lasting at least 2 hours, culturing the ICP under hypoxic conditions; and
during a non-hypoxic time period lasting at least 1 day, culturing the ICP under non-hypoxic conditions.

In an embodiment, the hypoxic and non-hypoxic time-periods are within a culturing time period lasting less than 30 days, and wherein culturing the ICP under hypoxic conditions includes culturing the cells under hypoxic conditions during a first two days of the culturing time period.

In an embodiment, the hypoxic and non-hypoxic time-periods are within a culturing time period lasting less than 30 days, and wherein culturing the ICP under hypoxic conditions includes culturing the ICP under hypoxic conditions during a last two days of the culturing time period.

In an embodiment, the hypoxic and non-hypoxic time-periods are within a culturing time period lasting less than 30 days, and wherein culturing the ICP under hypoxic conditions includes culturing the ICP under hypoxic conditions for at least 2 hours between a first two days and a last two days of the culturing time period.

In an embodiment, culturing the ICP under hypoxic conditions is performed prior to culturing the ICP under non-hypoxic conditions.

In an embodiment, culturing the ICP under hypoxic conditions is performed following culturing the ICP under non-hypoxic conditions.

In an embodiment, stimulating the ICP includes:
culturing the ICP in a first container during a first portion of a culturing period;
removing at least some cells of the ICP from the first container at the end of the first portion of the period; and
culturing, in a second container during a second portion of the period, the cells removed from the first container.

In an embodiment, the method includes, subsequently to the step of culturing in the second container:
culturing the ICP in a primary container during a first portion of an additional culturing period;
removing at least some cells of the ICP from the primary container at the end of the first portion of the additional period; and
culturing, in a secondary container during a second portion of the additional period, the cells removed from the primary container.

In an embodiment, stimulating the ICP includes:
culturing the ICP in a first container during a first portion of a culturing period;
removing cells of the ICP from the first container at the end of the first portion of the period; and
culturing, in a second container during a second portion of the period, the cells removed from the first container.

In an embodiment, removing at least some cells of the ICP includes selecting for removal cells that adhere to a surface of the first container.

In an embodiment, removing at least some cells of the ICP includes selecting for removal cells that do not adhere to a surface of the first container.

In an embodiment, the first container includes on a surface thereof a growth-enhancing molecule, and wherein culturing the ICP in the first container includes culturing the ICP in the first container that includes the growth-enhancing molecule.

In an embodiment, the growth-enhancing molecule is selected from the list consisting of: collagen, plasma, fibronectin, a growth factor, tissue-derived extra cellular matrix and an antibody to a stem cell surface receptor.

In an embodiment, the second container includes on a surface thereof a growth-enhancing molecule, and wherein culturing the ICP in the second container includes culturing the ICP in the second container that includes the growth-enhancing molecule.

In an embodiment, the growth-enhancing molecule is selected from the list consisting of: collagen, fibronectin, a growth factor, and an antibody to a stem cell surface receptor.

In an embodiment, stimulating includes culturing the ICP with at least one factor derived from a sample tissue.

In an embodiment, the method includes preparing a conditioned medium for culturing the ICP therein, the conditioned medium including the factor, the factor being derived from the tissue, the tissue being selected from the list consisting of: peripheral nerve tissue, central nervous system (CNS)

tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

In an embodiment, stimulating includes co-culturing the ICP with a sample tissue.

In an embodiment, co-culturing includes preparing the sample tissue by a method selected from the list consisting of: slicing the sample tissue, and homogenizing the sample issue.

In an embodiment, co-culturing includes:
utilizing the sample tissue to produce a conditioned medium; and
co-culturing the ICP with the sample tissue in the conditioned medium.

In an embodiment, co-culturing includes separating the sample tissue from the ICP by a semi-permeable membrane.

In an embodiment, the method includes designating the sample tissue to include a tissue selected from the list consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

There is further provided, in accordance with an embodiment of the invention, a method for treating a patient, including:
identifying a patient having a sexual dysfunction; and
administering angiogenic cell precursors to the patient, in order to treat the dysfunction.

There is also provided, in accordance with an embodiment of the present invention, a method including in vitro stimulating a core cell population (CCP) of at least 5 million cells that have a density of less than 1.072 g/ml, and at least 1% or at least 2% of which are CD34+CD45−/dim, to differentiate into a progenitor/precursor cell population (PCP).

For some applications, the CCP includes at least 5 million cells that have a density of less than 1.062 g/ml, at least 2% of which are CD34+CD45−/dim, and stimulating the CCP includes stimulating the CCP that has the at least 5 million cells that have a density of less than 1.062 g/ml.

For some applications, the method includes preparing the PCP as a product for administration to a patient. Alternatively, the method includes preparing the PCP as a research tool or a diagnostic tool.

For some applications, stimulating the CCP includes only stimulating the CCP if the CCP is derived from a mammalian donor. For some applications, the method includes applying cells extracted from a mammalian donor to one or more gradients suitable for selecting cells having a density less than 1.072 g/ml, and deriving the CCP from the cells applied to the gradient.

For some applications, the CCP is characterized by at least 2.5% of the CCP being CD34+CD45−/dim, and stimulating the CCP includes stimulating the CCP having the at least 2.5% of the CCP that are CD34+CD45−/dim. For some applications, the CCP is characterized by at least 50% of the CCP being CD14+, and stimulating the CCP includes stimulating the CCP having the at least 50% of the CCP that are CD14+. For some applications, the CCP is characterized by at least 40% of the CCP being CD14+, and stimulating the CCP includes stimulating the CCP having the at least 40% of the CCP that are CD14+.

For some applications, stimulating the CCP includes stimulating the CCP to differentiate into a pre-designated, desired class of progenitor cells.

For some applications, stimulating the CCP includes culturing the CCP during a period of between 3 and 30, 60, or 120 days.

For some applications, the method includes deriving the CCP from at least one source selected from the list consisting of: embryonic tissue, fetal tissue, umbilical cord blood, umbilical cord tissue, neonatal tissue, adult tissue, bone marrow, mobilized blood, peripheral blood, peripheral blood mononuclear cells, skin cells, and plant tissue. Alternatively, the method includes deriving the CCP from at least one source selected from the list consisting of: fresh tissue and frozen tissue. For some applications, the method includes identifying an intended recipient of the PCP, and deriving the CCP from at least one source selected from the list consisting of: tissue autologous to tissue of the intended recipient, tissue syngeneic to tissue of the intended recipient, tissue allogeneic to tissue of the intended recipient, and tissue xenogeneic to tissue of the intended recipient.

For some applications, stimulating the CCP includes incubating the CCP in a container having a surface including an antibody.

For some applications, stimulating the CCP includes incubating the CCP in a container having a surface including a plasma.

For some applications, stimulating the CCP includes culturing the CCP for a period lasting between 1 and 5, 10, or 20 days in a culture medium including less than 5% serum. For some applications, stimulating the CCP includes culturing the CCP for a period lasting between 1 and 5, 10, or 20 days in a culture medium including at least 10% serum.

For some applications, stimulating the CCP includes culturing the CCP in the presence of at least one of the following: erythropoietin, a statin, an antidiabetic agent, a thiazolidinedione, rosiglitazone, a proliferation-differentiation-enhancing agent, anti-CD34, anti-Tie-2, anti-CD133, anti-CD117, LIF, EPO, IGF, b-FGF, M-CSF, GM-CSF, TGF alpha, TGF beta, VEGF, BHA, BDNF, NGF, NT3, NT4/5, GDNF, S-100, CNTF, EGF, NGF3, CFN, ADMIF, prolactin, an adrenocorticoid, glutamate, serotonin, acetylcholine, NO, retinoic acid (RA), heparin, insulin, forskolin, cortisone, cortisol, dexamethasone, estrogen, a steroid, MCDB-201, sodium selenite, linoleic acid, ascorbic acid, transferrin, 5-azacytidine, PDGF, VEGF, cardiotrophin, and thrombin.

For some applications, the method includes preparing the CCP, and facilitating a diagnosis responsive to a characteristic of the preparation of the CCP.

For some applications, the method includes freezing the CCP prior to stimulating the CCP. For some applications, the method includes freezing the PCP.

For some applications, the method includes transporting the CCP to a site at least 10 km from a site where the CCP is first created, and stimulating the CCP at the remote site. For some applications, the method includes transporting the PCP to a site at least 10 km from a site where the PCP is first created.

In an embodiment, the method includes facilitating a diagnosis responsive to stimulating the CCP to differentiate into the PCP. For some applications, facilitating the diagnosis includes assessing an extent to which the stimulation of the CCP produces a particular characteristic of the PCP.

In an embodiment, the method includes transfecting a gene into the CCP prior to stimulating the CCP. For some applications, the method includes preparing, as a product for administration to a patient, the PCP generated by differentiation of the CCP into which the gene has been transfected.

In an embodiment, the method includes transfecting a gene into the PCP prior to administration of the PCP to a patient.

In an embodiment, stimulating the CCP includes incubating the CCP in a container with a surface including a growth-enhancing molecule other than collagen or fibronectin. For some applications, incubating the CCP cells includes incubating the CCP in a container having a surface that includes, in addition to the growth-enhancing molecule, at least one of: collagen, plasma and fibronectin. For some applications, the method includes mixing the growth-enhancing molecule with the at least one of: collagen, plasma and fibronectin. For some applications, the method includes applying to the surface a layer that includes the growth-enhancing molecule and a separate layer that includes the at least one of: collagen, plasma and fibronectin.

In an embodiment, stimulating the CCP includes:
during a low-serum time period, culturing the CCP in a culture medium including less than 10% serum; and
during a high-serum time period, culturing the CCP in a culture medium including greater than or equal to 10% serum.

For some applications, culturing the CCP during the low-serum time period includes culturing the CCP for a duration of between 1 and 5 or 20 days. For some applications, culturing the CCP during the high-serum time period includes culturing the CCP for a duration of between 1 and 30, 60, or 120 days. For some applications, culturing the CCP during the low-serum time period is performed prior to culturing the CCP during the high-serum time period. For some applications, culturing the CCP during the low-serum time period is performed following culturing the CCP during the high-serum time period.

In an embodiment, the method includes:
during a hypoxic time period lasting at least 2 hours, culturing the CCP under hypoxic conditions; and
during a non-hypoxic time period lasting at least 1 day, culturing the CCP under non-hypoxic conditions.

For some applications, the hypoxic and non-hypoxic time-periods are within a culturing time period lasting less than 120 days (e.g., less than 30 days), and culturing the CCP under hypoxic conditions includes culturing the cells under hypoxic conditions during a first two days of the culturing time period. For some applications, the hypoxic and non-hypoxic time-periods are within a culturing time period lasting less than 120 days (e.g., less than 30 days), and culturing the CCP under hypoxic conditions includes culturing the CCP under hypoxic conditions during a last two days of the culturing time period. For some applications, the hypoxic and non-hypoxic time-periods are within a culturing time period lasting less than 120 days (e.g., less than 30 days), and culturing the CCP under hypoxic conditions includes culturing the CCP under hypoxic conditions for at least 2 hours between a first two days and a last two days of the culturing time period.

For some applications, culturing the CCP under hypoxic conditions is performed prior to culturing the CCP under non-hypoxic conditions. Alternatively, culturing the CCP under hypoxic conditions is performed following culturing the CCP under non-hypoxic conditions.

In an embodiment, stimulating the CCP includes:
culturing the CCP in a first container during a first portion of a culturing period;
removing all or at least some cells of the CCP from the first container at the end of the first portion of the period; and
culturing, in a second container during a second portion of the period, the cells removed from the first container.

For some applications, removing at least some cells of the CCP includes selecting for removal cells that adhere to a surface of the first container. For some applications, removing at least some cells of the CCP includes selecting for removal cells that do not adhere to a surface of the first container.

For some applications, the first container includes on a surface thereof a growth-enhancing molecule, and culturing the CCP in the first container includes culturing the CCP in the first container that includes the growth-enhancing molecule.

For some applications, the growth-enhancing molecule is selected from the list consisting of: collagen, plasma, fibronectin, a growth factor, tissue-derived extra cellular matrix and an antibody to a stem cell surface receptor.

For some applications, the second container includes on a surface thereof a growth-enhancing molecule, and culturing the CCP in the second container includes culturing the CCP in the second container that includes the growth-enhancing molecule.

For some applications, the growth-enhancing molecule is selected from the list consisting of: collagen, plasma, fibronectin, a growth factor, tissue-derived extra cellular matrix and an antibody to a stem cell surface receptor.

In an embodiment, stimulating includes culturing the CCP with at least one factor derived from a target tissue. For some applications, the method includes preparing a conditioned medium for culturing the CCP therein, the conditioned medium including the factor, the factor being derived from a tissue selected from the list consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

In an embodiment, stimulating includes co-culturing the CCP with a tissue. For some applications, co-culturing includes preparing a target tissue by a method selected from the list consisting of: slicing the target tissue, and homogenizing the target issue. For some applications, co-culturing includes utilizing the target tissue to produce a conditioned medium, and co-culturing the CCP with the target tissue in the conditioned medium. For some applications, co-culturing includes separating the target tissue from the CCP by a semi-permeable membrane.

For some applications, the method includes designating a tissue for co-culture purposes to include a tissue selected from the list consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

There is also provided, in accordance with an embodiment of the present invention, a method including in vitro stimulating an elemental cell population (ECP) of at least 5 million cells that have a density of less than 1.072 g/ml, at least 1.5% of which are CD34+CD45−/dim, and at least 30% of which are CD14+, to differentiate into a progenitor/precursor cell population (PCP).

The present invention will be more fully understood from the following detailed description of embodiments thereof, taken together with the drawings, in which:

DETAILED DESCRIPTION OF EMBODIMENTS

Example 1

Figure 1:
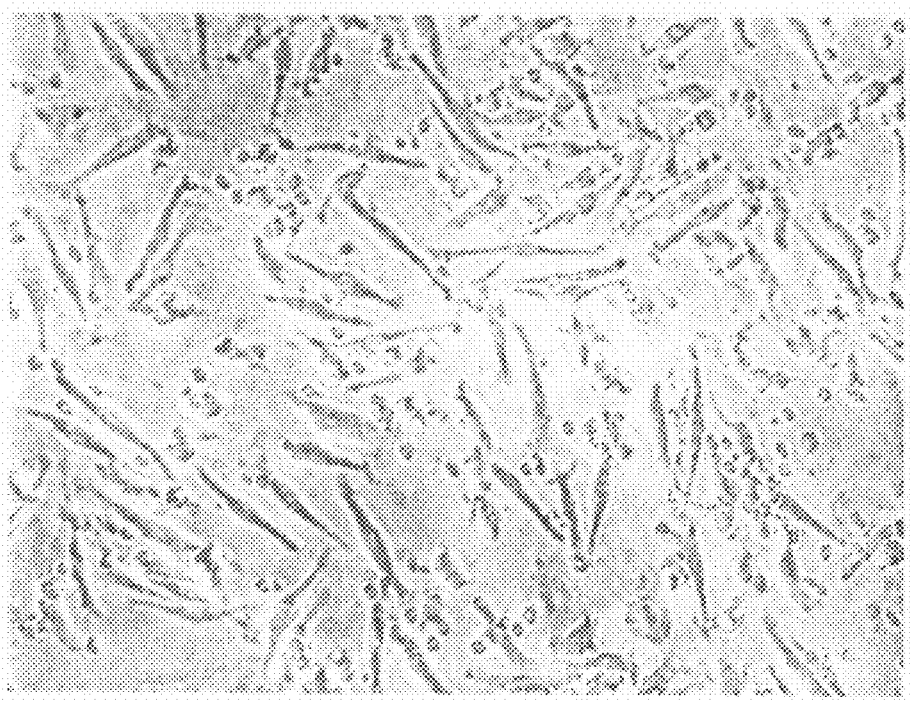
FIG. 1 is a photograph showing morphology of angiogenic cell precursor cells, produced in accordance with an embodiment of the present invention.

A test was carried out in accordance with an embodiment of the present invention, and results are shown in Table 1 below. Peripheral blood was extracted from ten human volunteers for use in ten respective experiments. In each experiment, a Ficoll gradient was used to generate a population of peripheral blood mononuclear (PBMC) cells as source cells ("S. cells"). Subsequently, a CCP was generated in accordance with protocols described herein for Percoll based enrichment. Results in Table 1 show enrichment of the percentages of CD14+ and CD34+CD45−/dim cells in the CCP compared to the source cells. Enrichment is defined as the percentage of cells having a given characteristic in the CCP divided by the percentage of cells having that characteristic in the source cells.

TABLE 1

| Exp No | % Viability | | % CD45 | | % CD14$^+$ | | | % CD34+ CD45−/dim | | |
|---|---|---|---|---|---|---|---|---|---|---|
| | S. cells | CCP | S. cells | CCP | S. cells | CCP | Enrichment factor | S. cells | CCP | Enrichment factor |
| 1 | 97.56 | 97.86 | 94.00 | 93.46 | 20.05 | 79.98 | 4.0 | 1.4 | 4.07 | 2.9 |
| 2 | 98.49 | 97.61 | 92.09 | 87.10 | 16.57 | 57.14 | 3.4 | 0.77 | 3.48 | 4.5 |
| 3 | 94.28 | 100 | 94.72 | 96.44 | 12.79 | 61.57 | 4.8 | 0.72 | 2.31 | 3.2 |
| 4 | 98.82 | 98.18 | 93.11 | 92.77 | 23.58 | 65.52 | 2.8 | 0.24 | 2.69 | 11.2 |
| 5 | 98.10 | 98.53 | 63.15 | 84.30 | 11.48 | 62.82 | 5.5 | 1.78 | 2.77 | 1.6 |
| 6 | 98.54 | 98.33 | 91.58 | 76.16 | 15.03 | 40.99 | 2.7 | 0.69 | 2.37 | 3.4 |
| 7 | 98.18 | 97.78 | 95.58 | 94.46 | 16.35 | 62.48 | 3.8 | 0.88 | 3.7 | 4.2 |
| 8 | 99.49 | 97.93 | 96.11 | 92.39 | 15.29 | 50.24 | 3.3 | 0.83 | 6.14 | 7.4 |
| 9 | 99.09 | 97.64 | 96.75 | 96.55 | 17.46 | 57.02 | 3.3 | 0.39 | 2.24 | 5.7 |
| 10 | 97.53 | 99.37 | 84.46 | 98.44 | 21.58 | 66.30 | 3.1 | 0.52 | 1.67 | 3.2 |
| Avg | 98.01 | 98.32 | 90.58 | 91.41 | 17.02 | 60.41 | 3.7 | 0.82 | 3.14 | 4.7 |

Example 2

In a separate set of experiments, in accordance with an embodiment of the present invention, results were obtained as shown in Table 2 below. Peripheral blood was extracted from ten human volunteers for use in ten experiments. A CCP was generated in accordance with protocols described herein (see Example 1). Results in Table 2 show enrichment of the percentages of CD31 cells in the CCP compared to the source cells. Enrichment is defined as the percentage of cells having a given characteristic in the CCP, divided by the percentage of cells having that characteristic in the source cell population.

TABLE 2

| | % CD31 | | |
|---|---|---|---|
| Exp No. | S. Cells | CCP | Enrichment Factor |
| 1 | 67.63 | 82.94 | 1.2 |
| 2 | 49.94 | 66.27 | 1.3 |
| 3 | 50.34 | 68.73 | 1.4 |
| 4 | 53.75 | 86.68 | 1.6 |
| 5 | 46.61 | 90.03 | 1.9 |
| 6 | 35.67 | 79.59 | 2.2 |
| 7 | 63.60 | 79.44 | 1.2 |
| 8 | 56.22 | 86.25 | 1.5 |
| 9 | 54.34 | 69.55 | 1.3 |
| 10 | 55.20 | 82.94 | 1.5 |
| Avg | 53.33 | 79.24 | 1.53 |

Example 3

In a separate set of experiments, a human-PBMC-derived CCP was cultured in order to generate an ACP-rich PCP. The CCP was grown on fibronectin or plasma-coated T75 flasks in the presence of medium containing autologous serum (>=10%), 2 ng/ml VEGF, and 5 IU/ml Heparin.

FIG. 1 is a photograph showing the morphology of a typical angiogenic cell precursor (ACP) population, produced in the experiments of Example 3 in accordance with an embodiment of the present invention. Typically, elongated and spindle-shaped cells are observed in cultures of ACPs. This image was obtained from ×200 magnification of cultured ACPs.

Example 4

In the same set of experiments, a human-PBMC-derived CCP was cultured in order to generate an ACP-rich PCP as described in Example 3. Flow-cytometry percentage staining results from ten independent experiments are summarized in Table 3. (Results for CD133, Tie-2, and CD117 were only measured in n=7, 6, and 6, of the experiments.) Table 3 shows the average staining results obtained on day 5 of culturing. Results using such a protocol typically yield a PCP having at least 20% ACPs, typically at least 45% ACPs.

TABLE 3

|  | Number experiments (n) | Average on day 5 | Standard Error |
|---|---|---|---|
| % Viability | 10 | 93.84 | 0.63 |
| % CD45 | 10 | 94.29 | 1.46 |
| % CD14 | 10 | 70.69 | 3.56 |
| % CD34 | 10 | 23.09 | 4.98 |
| % CD34 + CD45−/dim | 10 | 4.19 | 1.34 |
| CD34 + CD14−/dim | 10 | 3.42 | 0.73 |
| % KDR | 10 | 8.90 | 4.49 |
| % CD133 | 7 | 0.28 | 0.18 |
| % Tie-2 | 6 | 24.84 | 11.46 |
| % CD117 | 6 | 10.82 | 4.60 |
| % ACPs in product | 10 | 49.43 | 11.44 |

Example 5

In a separate set of experiments, a human-PBMC-derived CCP was cultured in order to generate an ACP-rich PCP as described in Example 3. Secretion levels (pg/ml) of IL-8, VEGF, and angiogenin from four independent experiments are summarized in Table 4. Table 4 shows the average secretion levels obtained from harvested ACP-rich PCP cells that were washed from culture medium and incubated for 24 hours in a serum-free medium.

TABLE 4

| Group | IL-8 pg/ml | VEGF pg/ml | Angiogenin pg/ml |
|---|---|---|---|
| Control Medium | ≤20 | ≤20 | ≤20 |
| ACP derived medium | 10107 | 165 | 615 |

Example 6

In the same set of experiments, a human-PBMC-derived CCP was cultured in order to generate an ACP-rich PCP as described in Example 3. Angiogenic pattern and vascular tube formation of ACP-rich PCP cells was examined microscopically following plating of the cells on an extracellular matrix gel (ECM). Typically, semi-closed and closed polygons of capillaries and complex mesh-like capillary structures were observed and scored (according to a scale published by Kayisli et al. (52) as grade 4-5.

Figure 2:
FIG. 2 is a photograph showing tube formation in an ACP-rich PCP, produced in accordance with an embodiment of the present invention.

FIG. 2 is a photograph showing tube formation in an ACPs, produced in the experiments of Example 6, in accordance with an embodiment of the present invention. The figure shows typical mesh-like capillary structures generated from a harvested ACPs, suitable for administration to a human.

Example 7

In a separate set of experiments, a human-PBMC-derived CCP was cultured in order to generate an ACP-rich PCP as described in Example 3. The ACP-rich PCP therapeutic potential was assessed in a rat model of acute myocardial infarction. Myocardial infarction was induced in 15 male nude rats (200-225 g) by ligation of the left anterior descending (LAD) artery. Six days after myocardial infarction, the rats were injected with $1.5 \times 10^6$ ACP-enriched cells (ACP, n=10) or culture medium (Control, n=5), via the aortic arch. Cardiac function (ejection fraction) and the ratio of necrotic scar area to left ventricular free wall area were measured 28 days following ACP-rich PCP or culture medium administration. Paraffin fixed tissue sections were stained in order to trace engrafted human cells and CMC markers in the border area of the scar tissue.

Figure 3A:
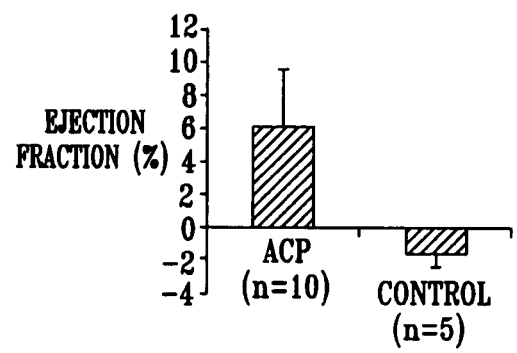
FIGS. 3A and 3B are graphs showing improved ejection fraction and reduced necrosis, produced in accordance with an embodiment of the present invention.
Figure 3B:
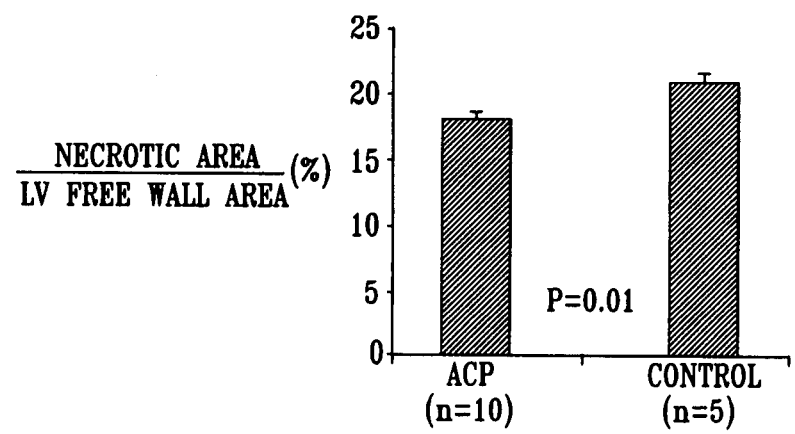

FIGS. 3A and 3B are graphs showing results obtained in the experiments of Example 7, in accordance with an embodiment of the present invention. ACPs derived from a human-PBMC-derived CCP are seen to show a beneficial effect in this rat model of acute myocardial infarction.

Figure 3C:
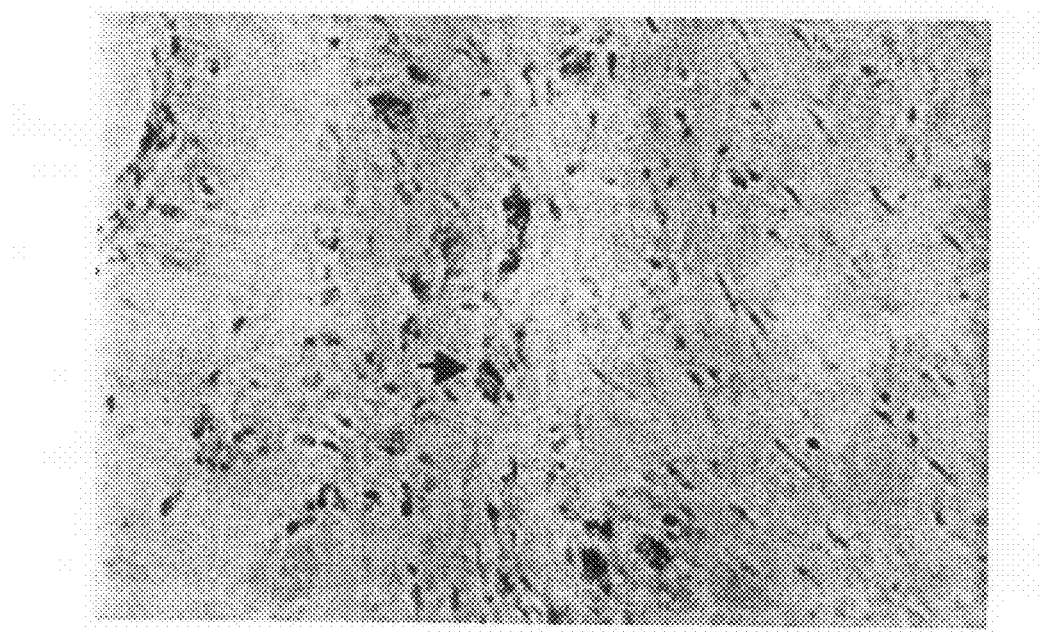
FIGS. 3C, 3D, and 3E are photographs showing sections taken from a rat's heart after implantation of ACPs derived from a human-PBMC-derived CCP, produced in accordance with an embodiment of the present invention.
Figure 3D:
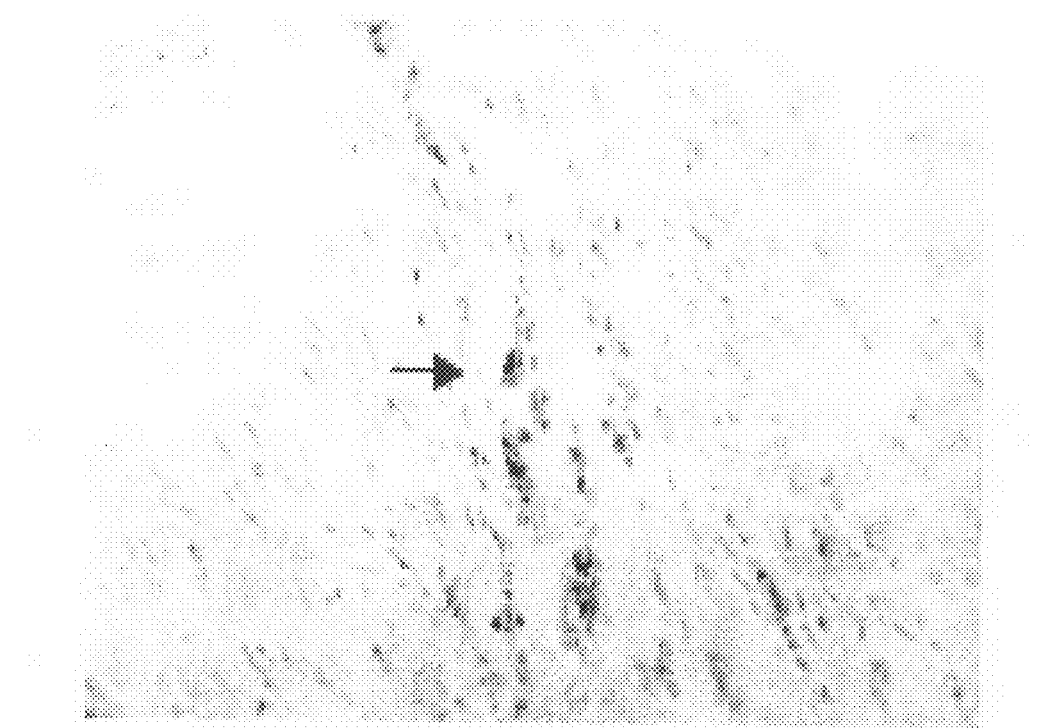
Figure 3E:
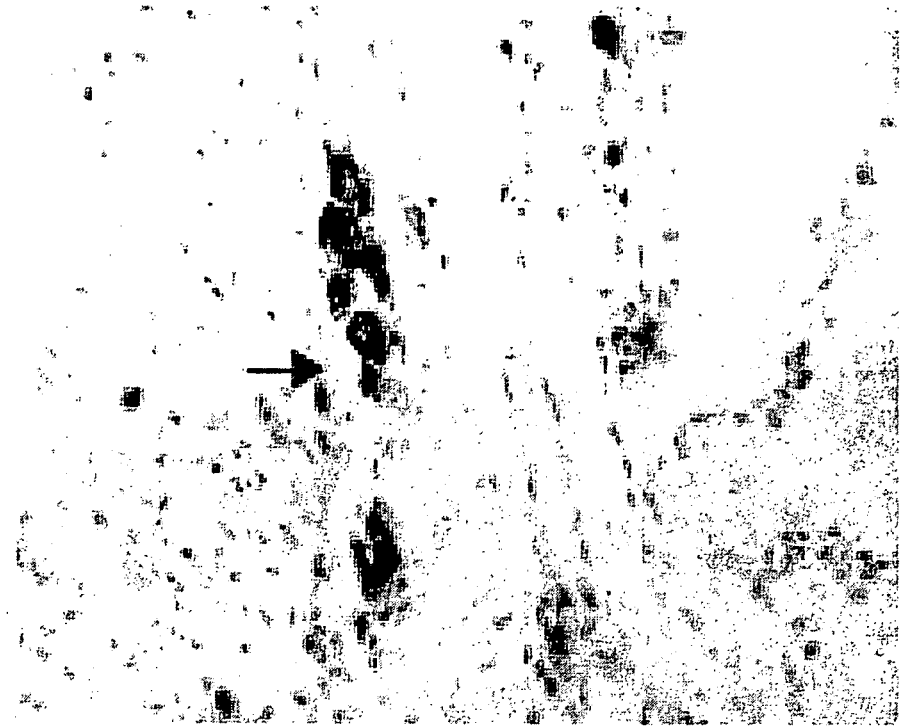

FIGS. 3C, 3D and 3E are photographs showing typical sections taken from a rat's heart 28 days after the implantation of ACPs derived from a human-PBMC-derived CCP in the experiments of Example 7, in accordance with an embodiment of the present invention. Anti-human mitochondria (FIG. 3C) and the CMC markers myosin heavy chain (MHC) (FIG. 3D) and cardiac Troponin I (FIG. 3E) stained cells are marked by arrows. These results demonstrate that human ACPs, derived in accordance with an embodiment of the present invention, homed to damaged cardiac tissues, engrafted, and transdifferentiated into cells expressing cardiomyocyte markers. The inventors hypothesize that these processes of engraftment and transdifferentiation explain the beneficial effects demonstrated in the rat model of acute MI (improved ejection fraction and reduced necrosis).

The inventors therefore hypothesize that ACPs improve systemic endothelial functioning. Particular examples of improvement due to administration of ACPs, derived in accordance with an embodiment of the present invention, include improved cardiovascular functioning and improved sexual functioning. The scope of the present invention includes identifying a patient having cardiovascular dysfunction or sexual dysfunction, and administering ACPs to the patient in order to treat the dysfunction.

Example 8

In a separate set of experiments, a human-PBMC-derived CCP was cultured in order to generate a cardiomyocyte (CMC)-rich PCP. The CCP was grown on fibronectin or plasma-coated T75 flasks in accordance with protocols described herein (see medium preparation).

Figure 4:
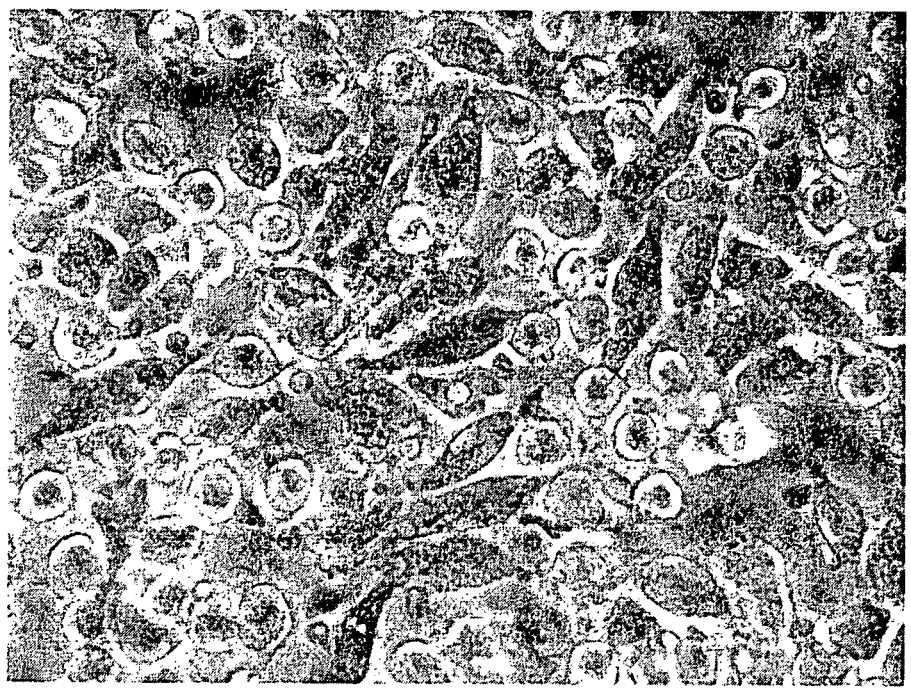
FIG. 4 is a photograph showing cardiomyocyte morphology, produced in accordance with an embodiment of the present invention.

FIG. 4 is a photograph of a typical CMC-rich PCP from the experiments of Example 8, derived in accordance with an embodiment of the present invention. Typically, these cells appeared elongated with dark cytoplasm, which may indicate high protein content. This image was obtained from ×200 magnification of cultured CMC PCP cells.

Figure 5A:
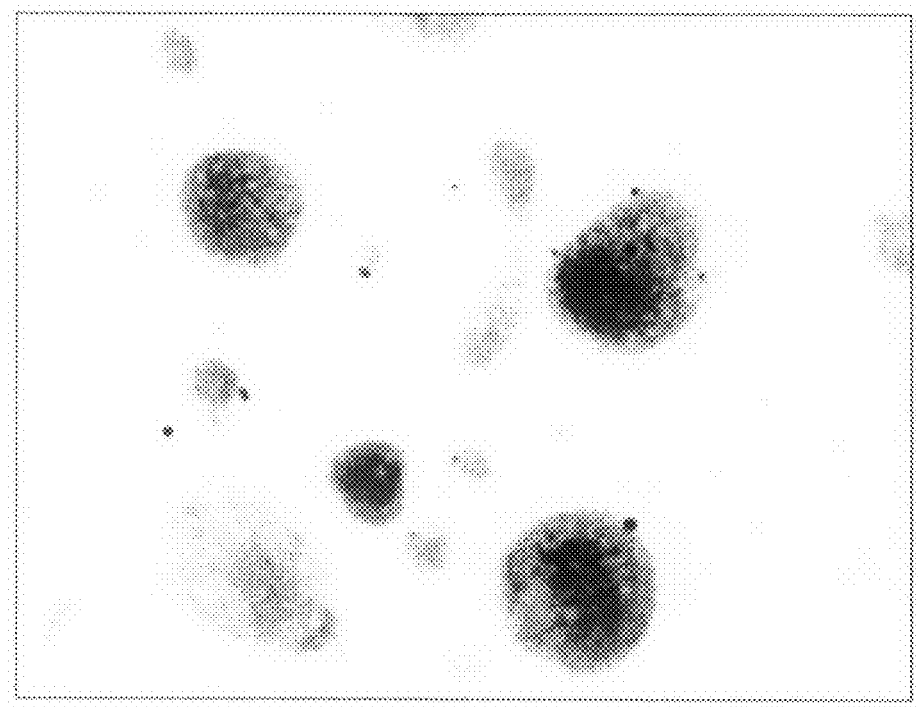
FIGS. 5A, 5B, and 5C are photographs showing immunostaining of CCP-derived cardiomyocytes, in accordance with an embodiment of the present invention.
Figure 5B:
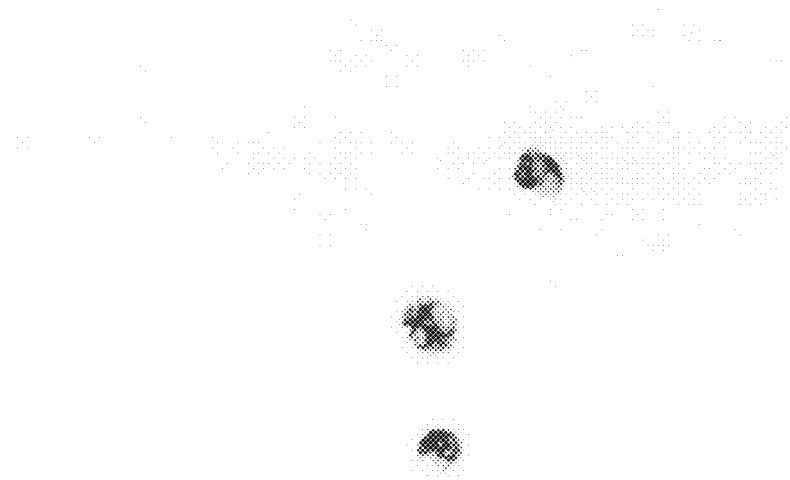
Figure 5C:
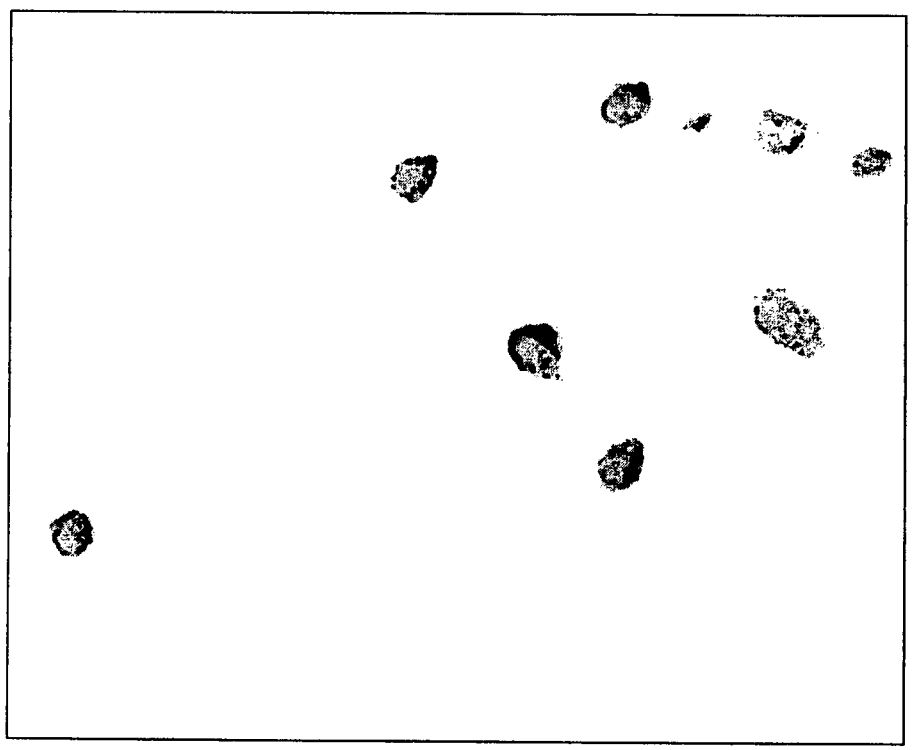

FIGS. 5A, 5B, and 5C are photographs showing immunostaining of CCP-derived cardiomyocytes in the experiments of Example 8, in accordance with an embodiment of the present invention. Slide-fixed CMC PCP cells were stained with:

FIG. 5A—Anti-cardiac Troponin detected by anti mouse Cy-3;

FIG. 5B—Anti-α-actin detected by anti-mouse IgG-FITC; and

FIG. 5C—Anti-Connexin 43 detected by anti-mouse IgG-FITC.

Cells stained with non-specific mouse IgG were detected by anti-mouse IgG-FITC or by anti-mouse IgG-Cy3 used as negative controls.

The images in FIG. 5 show that CMC PCP cells expressed the typical cardiomyocyte cellular markers cardiac Troponin T (FIG. 5A), α-actin (FIG. 5B), as well as the functionally important GAP junction marker Connexin-43 (FIG. 5C). Images were obtained from ×100 magnification of slide-fixed cells.

Example 9

In the same set of experiments that produced the results shown in FIGS. 4 and 5, a human-PBMC-derived CCP was cultured in order to generate a CMC-rich PCP. The CCP was grown on fibronectin or plasma-coated T75 flasks in accordance with protocols described herein (see medium preparation).

Figure 6A:
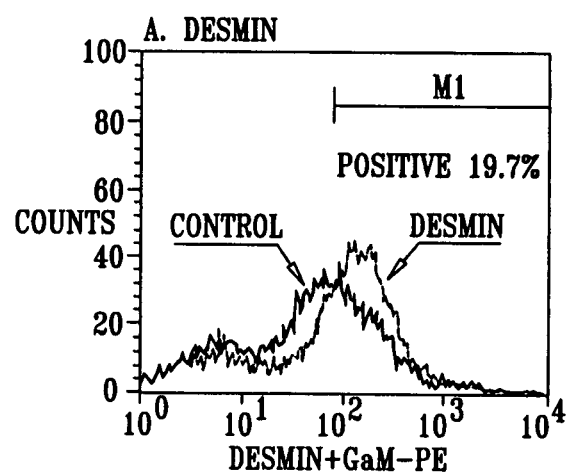
FIGS. 6A and 6B are graphs showing flow cytometry analysis results, obtained from immunostaining of a cardiomyocyte-rich PCP, in accordance with an embodiment of the present invention.
Figure 6B:
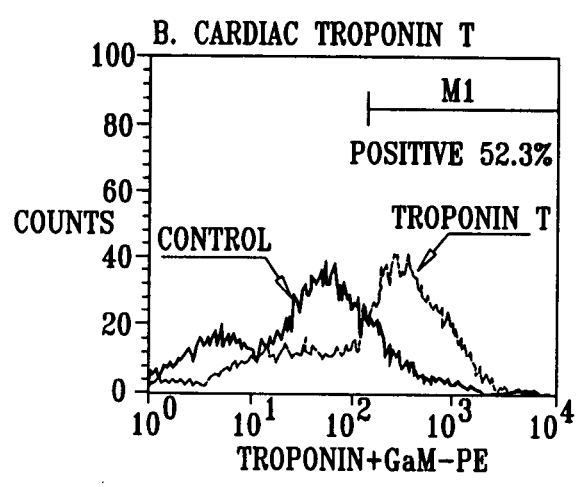

FIGS. 6A and 6B are graphs showing flow cytometry analysis results, obtained from immunostaining of a cardiomyocyte-rich PCP in the experiments of Example 9, in accordance with an embodiment of the present invention. In FIG. 6, lines describing control non-specific staining are marked as Control, specific immunostaining with the cardiac cellular markers desmin and Troponin T are marked as Desmin (FIG. 6A) and Troponin T (FIG. 6B). The MI line represents the statistical marker area in which the percentage of cells that positively stained is measured.

Example 10

In a separate set of experiments, a human-PBMC-derived CCP was cultured in order to generate a CMC-rich PCP. The CCP was grown on fibronectin or plasma-coated T75 flasks in accordance with protocols described herein (see medium preparation). The CMC PCP cells' therapeutic potential was assessed in the rat model of acute myocardial infarction. CMC PCP cells were used for implantation into a rat model of acute myocardial infarction as described in Example 7. Six days after myocardial infarction, the rats were injected with $1.5\times10^{\wedge}6$ CMC PCP cells (CMC, n=9) or culture medium (Control, n=5), into the heart muscle. Cardiac function (ejection fraction) was tested 14 days following the administration of CMC PCP cells or culture medium.

Figure 7:
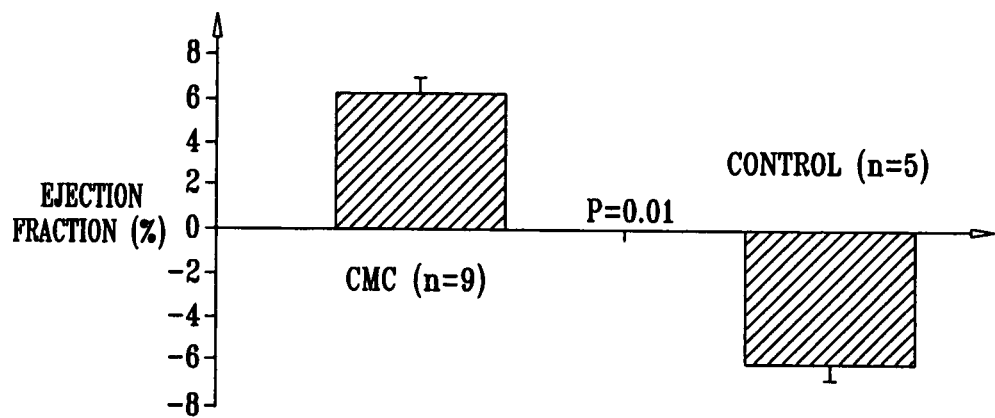
FIG. 7 is a graph showing improved ejection fraction results in a rat model of acute myocardial infarction, in accordance with an embodiment of the present invention.

FIG. 7 is a graph showing experimental results obtained in the experiments of Example 10, in accordance with an embodiment of the present invention. CMC PCP cells, derived in accordance with an embodiment of the present invention, are seen to show beneficial effect in the rat model of acute myocardial infarction.

A series of protocols are described hereinbelow which may be used separately or in combination, as appropriate, in accordance with embodiments of the present invention. It is to be appreciated that numerical values are provided by way of illustration and not limitation. Typically, but not necessarily, each value shown is an example selected from a range of values that is within 20% of the value shown. Similarly, although certain steps are described with a high level of specificity, a person of ordinary skill in the art will appreciate that other steps may be performed, mutatis mutandis.

In accordance with an embodiment of the present invention, generation of a single-cell suspension is carried out using the following protocol:

Example 1

Extraction of Peripheral Blood Mononuclear Cells (PBMC)

Receive blood bag and sterilize it with 70% alcohol
Load blood cells onto a Ficoll gradient.
Spin the tubes for 20 minutes at 1050 g at room temperature (RT), with no brake.
Collect most of the plasma from the upper layer.
Collect the white blood cell fraction from every tube.
Transfer the collected cells to a new 50 ml tube, adjust volume to 30 ml per tube using PBS.
Spin tubes for 15 minutes at 580 g, RT, and discard supernatant.
Count cells in Trypan blue.
Re-suspend in culture medium comprising, for example, X-vivo 15™.

Example 2

Extraction of Cells from Umbilical Cord

Take 10 cm umbilical cord.
Wash thoroughly with sterile PBS.
Identify the big vein of the cord, and close one end of the vein using clamps.
Wash twice with 30 ml sterile PBS.
Fill vein with 0.15% collagenase (about 5 ml of 0.15% collagenase solution).
Close the second end of the vein using clamps.
Incubate at 37° C. for 15 min.
Wash outer side of the cord with 70% ethanol.
Untie the clamps from one end and collect cell suspension.
Centrifuge for 10 min at 580 g, 21° C.
Re-suspend in culture medium comprising, for example, X-vivo 15™, 10% autologous serum, 5 IU/ml heparin, and one or more growth factors.

Example 3

Extraction of Cells from Bone Marrow

Get bone marrow aspiration from surgical room
Re-suspend in culture medium comprising, for example, X-vivo 15™, 10% autologous serum, 5 IU/ml heparin, and one or more growth factors.
Pass suspension through a 200 μm mesh.

In accordance with an embodiment of the present invention, generation of a CCP is carried out using the following protocol:

Example 1

Generation of a Human CCP from PBMCs Using a Percoll Gradient

Prepare gradient by mixing a ratio of 5.55 Percoll (1.13 g/ml):3.6 ddH2O:1 PBS×10.
For every 50 ml tube of Percoll: mix 20 ml of Percoll stock, 13 ml of ddH2O and 3.6 ml of PBS×10.

Mix vigorously, by vortexing, for at least 1 min.
Load 34 ml mix into each 50 ml tube.
Centrifuge tubes, in a fixed angle rotor, for 30 min at 17,000 g, 21° C., with no brake.
Gently layer 3.0 ml of cell suspension of 150 million-400 million PBMCs on top of the gradient.
Prepare a second tube with density marker beads: gently layer 3.0 ml of medium on top of the gradient.
Gently load density marker beads—10 µl from each bead type.
Centrifuge tubes, in a swinging bucket rotor, for 30 min at 1260 g at 13° C., with no brake.
Gently collect all bands located above the red beads, and transfer to tube with 10 ml medium.
Centrifuge cells for 15 min at 580 g at 21° C.
Discard supernatant and re-suspend pellet in medium.
Count cells in Trypan blue.
Centrifuge cells for 10 min at 390 g, 21° C.
Discard supernatant and re-suspend pellet in medium.
Take CCP cells for FACS staining.

Example 2

Generation of Human CCP from PBMCs Using an OptiPrep Gradient

Take up to 130 million cells for each enrichment tube.
Spin cells for 10 min at 394 g, 21° C.
Suspend cell pellet in 10 ml of donor serum.
Prepare a 1.068 g/ml OptiPrep gradient by mixing a ratio of 1 OptiPrep:4.1 PBS.
For every 50 ml enrichment tube:
Mix 10 ml of cell suspension with 4 ml OptiPrep.
For preparation of a 1.068 g/ml OptiPrep gradient, mix 5 ml of OptiPrep and 20.5 ml of PBS.
Gently layer 20 ml of the 1.068 g/ml gradient on top of the cell suspension.
Gently layer 1.5 ml Hank's buffered saline (HBS) on top of the gradient layer.
Centrifuge for 30 min at 700 g at 4° C., with no brake.
Gently collect the layer of cells that floats to the top of the 1.068 g/ml OptiPrep gradient into a 50 ml tube pre-filled with PBS.
Centrifuge for 10 min at 394 g, 21° C.
Discard supernatant and re-suspend pellet in medium.
Count cells in Trypan blue.
Culture containers are either un-coated or coated with one or a combination of ACP-enhancing materials such as collagen, fibronectin, CD34, CD133, Tie-2, or anti-CD117.
In accordance with an embodiment of the present invention, the coating of a tissue culture container is carried out using the following protocol:

Example 1

Coating T75 Flasks with 25 µg/ml Fibronectin

For 20 T75 flasks—Prepare up to seven days before, or on day of PBMC preparation.
Prepare 50 ml of 25 µg/ml fibronectin solution in PBS.
Fill every flask with 2-5 ml fibronectin 25 µg/ml.
Incubate at 37° C. for at least 30 min.
Collect fibronectin solution.
Wash flask twice in PBS.
Dry flasks
Keep dry flasks at room temperature.
Dried flasks can be saved for one week at room temperature (RT).

Example 2

Coating T75 Flasks with 25 µg/ml Fibronectin and 5 ng/ml BDNF

Coat flasks with Fibronectin 25 µg/ml, as described in Example 1.
Prepare 50 ml of 5 ng/ml BDNF solution in PBS.
After washing off Fibronectin, fill every flask with 2-5 ml BDNF 10 ng/ml.
Incubate at 37° C. for 1 hour.
Collect the solution.
Wash flask twice in 10 ml PBS.
Keep dry flasks at room temperature until use.
In accordance with an embodiment of the present invention, serum preparation is carried out using the following protocol:
Serum can be obtained directly or prepared from plasma.

Example

Preparation of Serum from Human Plasma

Take 100 ml of undiluted blood.
Spin at 1100 g (2500 rpm) for 10 min.
Transfer the upper layer (plasma) to a new 50 ml tube.
Add 1.0 ml 0.8 M $CaCl_2$-$2H_2O$ for every 40 ml plasma.
Incubate for 0.5-3 hours at 37° C.
Spin coagulated plasma 5 min at 2500 g.
Collect the serum in a new tube, avoiding clotting.
Aliquot collected serum and save at −20° C. until use.
In accordance with an embodiment of the present invention, medium preparation is carried out using the following protocol:
Medium should contain 1-20% autologous serum and/or 1-20% conditioned medium.
Medium can contain one or more additives, such as LIF, EPO, IGF, b-FGF, M-CSF, GM-CSF, TGF alpha, TGF beta, VEGF, BHA, BDNF, NGF, EGF, NT3, NT4/5, GDNF, S-100, CNTF, NGF3, CFN, ADMIF, estrogen, progesterone, cortisone, cortisol, dexamethasone, or any other molecule from the steroid family, prolactin, an adrenocorticoid, glutamate, serotonin, acetylcholine, NO, retinoic acid (RA), Heparin, insulin, forskolin, Simvastatin, MCDB-201, sodium selenite, linoleic acid, ascorbic acid, transferrin, 5-azacytidine, PDGF, VEGF, cardiotrophin, and thrombin, or Rosiglitazone in various concentrations, typically ranging from about 100 pg/ml to about 100 µg/ml (or molar equivalents).
Typically, medium should not be used more than 10 days from its preparation date.

Example 1

Medium for Enhancement of CCP-Derived Angiogenic Cell Precursors (ACPs)

Serum-free medium (e.g., X-vivo 15™)
10% autologous serum
5 IU/ml Heparin
5 ng/ml VEGF
1 ng/ml EPO Example 2

Medium for Enhancement of CCP-Derived Neuronal Progenitor Cells

Serum-free medium (e.g., X-vivo 15™)
20 ng/ml bFGF 50 ng/ml NGF
200 μM BHA (this is added during the last 24 hours of culturing)
10 μM forskolin
1 μM cortisone
1 μg/ml insulin Example 2.1

Medium for Enhancement of CCP-Derived Neuronal Progenitor Cells

Serum-free medium (e.g., X-vivo 15™)
20 ng/ml bFGF
50 ng/ml NGF
25 ng/ml BDNF
200 μM BHA (this is added during the last 24 hours of culturing)

Example 3

Medium for Enhancement of CCP-Derived Retinal Cells

Serum-free medium (e.g., X-vivo 15™)
10% autologous serum
5 IU/ml Heparin
10 ng/ml EGF
20 ng/ml bFGF
50 ng/ml NGF3

Example 4a

Medium for Enhancement of CCP-Derived Cardiomyocyte (CMC) Progenitor Cells

Step I
Serum-free medium (e.g., X-vivo 15 ™)
10% autologous serum
20 ng/ml bFGF
5 IU heparin.
Step II
Five to ten days after culture onset, add 3 μM 5-azacytidine for 24 hours.

Example 4b

Medium for Enhancement of CCP-Derived CMC Progenitor Cells

Serum free medium DMEM-Low glucose
20% autologous serum
10% MCDB-201
2 μg/ml Insulin
2 μg/ml Transferin
10 ng/ml Sodium Selenite
50 mg/ml BSA
1 nM Dexamethasone
0.47 ug/ml Linoleic acid
0.1 mM Ascorbic Acid
100 U/ml penicillin In accordance with an embodiment of the present invention, conditioned medium preparation is carried out using the following protocol:

Example 1

Preparation of 100 ml Enriched Medium Containing 10% Autologous Conditioned Medium Thaw 10 ml conditioned medium in an incubator.
When thawed, add it to culture medium using pipette.
Extraction of Tissue Pieces for Co-Culture
Dissection of Rat Blood Vessels (Other Non-Human or Human Tissues May Also be Used):
Anesthetize animal using anesthetic reagents (e.g., 60-70% CO2, isoflurane, benzocaine, etc.).
Lay animal on its back and fix it to an operating table.
Using sterile scissors, cut animal's skin and expose the inner dermis.
Using a second set of sterile scissors, cut the dermis, cut chest bones, and expose the heart and aorta.
Cut small pieces, 0.2-1 cm long, from the aorta and other blood vessels, and place them in a container pre-filled with 50 ml cold culture medium (e.g. RPMI, X-vivo 15™, or any other growth medium).
Using forceps and scissors, clean tissue sections, to remove outer layers such as muscle, fat, and connective tissue.
Using forceps and scalpel, cut each blood vessel along its length, and expose the inner layer of endothelial cells.
Using forceps and scalpel, cut small pieces of up to 0.1 cm2 from the tissue.
It is to be understood that whereas this technique is in accordance with one embodiment of the present invention, the scope of the present invention includes extracting a blood vessel from a human, as well. For example, an incision may be made over the saphenous vein, in order to facilitate dissection of a distal 1 cm portion of the vein. Tributary veins thereto are tied and transected. Distal and proximal ends of the 1 cm portion of the saphenous vein are tied, and the vein is harvested.
Use the dissected tissue for direct and/or indirect co-culturing with the CCP and/or to generate conditioned medium.
Generation of Conditioned Medium
Lay dissected pieces in culture containers, for example in T75 flasks, or 50 ml tubes.
Optionally, fill with cell culture medium containing 0.1-3 μg/ml or 3-100 μg/ml apoptotic reagent (such as valinomycin, etoposide or Staurosporine), until all pieces are covered.
Refresh culture medium every 2 days.
Collect this medium (now conditioned medium) into 50 ml tubes.
Spin collected conditioned medium at 450 g for 10 min, at room temperature.
Collect supernatant in a new sterile container.
Details regarding preservation of the conditioned medium, in accordance with an embodiment of the present invention, are described hereinbelow.
In accordance with an embodiment of the present invention, culturing of a CCP to produce a PCP is carried out using the following protocol:

Example 1

Culturing of CCP Cell Suspension in T75 Flasks

Spin suspension for 15 minutes at 450 g, 21° C.
Discard the supernatant.

Gently, mix cell pellet and re-suspend the CCP cells.
Re-suspend pellet to 10 million CCP cells/ml.
Fill T75 flask with 15 ml enriched medium, and add 5 ml of 10 million CCP cells/ml to attain a final concentration of 50 million CCP cells/flask.
Incubate T75 flasks, plates and slides at 37° C., 5% CO2.

Example 2

Applied Hypoxia

For some applications, increased expansion and/or differentiation of the CCP may be obtained by exposure of the cell culture to oxygen starvation, e.g., 0.1-5% or 5-15% oxygen (hypoxia), for 2-12 or 12-48 hours. This is typically done one or more times, at different points during cell culturing.
Incubate T75 flasks in an oxygen-controlled incubator.
Set the oxygen pressure at 0.1%, and maintain it at this level for 24 hours.
Remove the flasks from the incubator and examine the culture.
Take a sample of CCP cells and test viability by Trypan blue exclusion method.
Set the oxygen pressure of the incubator at 20%.
Re-insert the flasks into the incubator and continue incubation for the rest of the period. This procedure can be repeated, for example, once a week during the culture period and/or within 24, 48, or 72 hours before termination of the culture.

Example 3

Reseeding of Adherent and/or Detached and/or Floating Cells

For some applications, increased expansion and differentiation of the CCP may be achieved by re-seeding collected cells on new pre-coated dishes in culture medium.
Collect all cultured CCP in tubes.
Spin tubes for 10 minutes at 450 g, 21° C.
Discard the supernatant.
Gently mix pellet and re-suspend cells in 10 ml fresh medium per T75 flask.
Seed suspended cells in new pre-coated T75 flasks.
Continue culturing the cells, and perform all other activities (e.g., medium refreshment, visual inspection, and/or flow cytometry), as appropriate, as described herein.
This procedure can be performed weekly during the culture period and/or within 24, 48, or 72 hours before termination of the culture.
In accordance with an embodiment of the present invention, co-culturing of CCP with tissue-derived conditioned medium is carried out using the following protocol:

Example 1

Culturing of CCP in the Presence of Conditioned Medium Derived from a Blood Vessel Culture Spin CCP cells for 15 minutes at 500 g, 21° C.
Discard the supernatant.
Gently mix cell pellet and re-suspend cells to 5-50 million/ml in autologous medium containing 1-20% autologous serum and/or 1-20% conditioned medium.
Seed flasks with 2-5 million CCP cells/ml.
Incubate flasks at 37° C., 5% CO2.
After first three days of culture, non-adherent cells can be removed from the culture.
In accordance with an embodiment of the present invention, refreshing of the media in ongoing growing CCP cultures is carried out using the following protocol:
Refreshing of the media in ongoing growing flasks should occur every 3-4 days.

Example 1

Refreshing of Medium in T-75 Flasks

Collect non-adherent cells in 50 ml tubes.
Fill every flask with 10 ml fresh culture medium enriched with conditioned medium.
Spin tubes for 10 minutes at 450 g, RT; discard the supernatant.
Gently mix cell pellet and re-suspend cells in 10 ml/flask fresh culture medium enriched with condition medium.
Return 5 ml of cell suspension to every flask.
In accordance with an embodiment of the present invention, indirect co-culture of CCP cells with tissue dissection is carried out using the following protocol:
Co-Culture in Separate Chambers within a Culture Container Example Indirect Co-Culture of Dissected Blood Vessel and CCP Cells in a Semi-Permeable Membrane Apparatus Lay dissected tissue pieces in the upper chamber of the apparatus on top of the semi-permeable membrane.
Implant CCP cells in lower chamber.
Lower chamber can be pre-coated with growth-enhancing molecules such as collagen, plasma, fibronectin, a growth factor, tissue-derived extra cellular matrix and an antibody.
Refresh culture medium in the upper chamber—aspirate conditioned medium into 50 ml tubes and add autologous culture medium.
Preserve collected conditioned medium at −20° C.
Remove upper chamber after four days of co-culture.
Refresh culture medium of the CCP cells with culture medium containing 1-20% autologous serum and/or 1-20% conditioned medium.
Continue growing and harvesting as described herein.
Co-Culture in Separate Chambers within a Culture Container
In accordance with an embodiment of the present invention, co-culturing within a culture container is carried out using the following protocol:

Example 1

Direct Co-Culturing of Autologous Dissected Blood Vessel and CCP Cells

Lay dissected tissue pieces in pre-coated flasks.
Implant CCP cells in pre coated second chamber.
Using forceps, take out tissue pieces after four days of co-culture.
Refresh culture medium of the CCP cells with culture medium containing 1-20% autologous serum and/or 1-20% condition medium.
Continue growing and harvesting as described herein.
In accordance with an embodiment of the present invention, harvesting of the cellular product is carried out using the following protocol:

Example 1

Collection of Resulting ACP Cultures

Collect cells in 50 ml tubes.

Carefully wash flask surface by pipetting with cold PBS to detach adherent cells.

Collect washed adherent cells to 50 ml tubes.

Add 5 ml of cold PBS.

Detach remaining adherent cells using gentle movements with cell scraper.

Collect the detached cells and add them to the tubes

Optionally, add 5 ml EDTA to each flask and incubate at 37° C. for 5 min.

Collect the detached cells and add them to the tubes Spin tubes for 5 min, at 450 g, room temperature.

Re-suspend the pellets in 2-5 ml PBS.

Count the cells in Trypan blue.

In accordance with an embodiment of the present invention, cellular product preservation is carried out using the following protocol:

Cellular product can be kept in preservation media or frozen in freezing buffer until use for transplantation into a patient.

Example 1

Cryopreservation of Cellular Product

Prepare freezing buffer containing 90% human autologous serum and 10% DMSO.

Suspend cellular product in freezing buffer and freeze in liquid nitrogen.

Example 2

Short-Period Preservation of Cellular Product

Prepare preservation medium including growth medium containing 1-20% autologous serum, with few or no other additives. Maintain preservation medium with cellular product at 2-12° C.

In accordance with an embodiment of the present invention, conditioned medium collection and preservation is carried out using the following protocol:

Conditioned medium can be kept until use for growth medium preparation.

Conditioned medium should be collected under sterile conditions.

Spin collected conditioned medium for 10 min at 450 g, 21° C.

Collect supernatant in a new sterile container.

Filter supernatant through a 22 μm membrane.

Aliquot conditioned medium to 10 and/or 50 ml sterile tubes, pre-marked with donor details.

Keep at −20° C. until use.

In accordance with an embodiment of the present invention, FACS staining is carried out using the following protocol:

Example 1

Staining of ACP Enriched Population

FACS Staining Protocol:

| Tube No. | Staining | Aim of staining |
|---|---|---|
| 1 | Cells | Un-stained control |
| 2 | CD45 (IgG1)-FITC | Single staining for PMT and compensation settings |
| 3 | CD14-PE (IgG2a) | |
| 4 | CD45 (IgG1)-APC | |
| 5 | mIgG1-FITC | Isotype control |
|   | mIgG1-PE | |
|   | mIgG1-APC | |
| 6 | CD45-FITC (IgG1) | |
|   | KDR-PE (IgG2a) | |
|   | CD34-APC (IgG1) | |
| 7 | mIgG1-FITC | Isotype control |
|   | mIgG2a-PE | |
|   | mIgG1-APC | |
| 8 | CD45-FITC (IgG1) | |
|   | CD133-PE (IgG2a) | |
|   | CD34-APC (IgG1) | |

Example 2

Staining of CMC Progenitors

FACS Staining Protocol for Fixed Permeabilized Cells:

| Tube No. | Staining 1st step | Staining 2nd step | Aim of staining |
|---|---|---|---|
| 1 | Cells | | Un-stained control |
| 2 | CD45-FITC (IgG1) | | Single staining for PMT and compensation settings |
| 3 | CD14-PE (IgG2a) | | |
| 5 | mIgG1 | Anti mouse-PE | Isotype control |
| 6 | Desmin | Anti mouse-PE | |
| 7 | Troponin T | Anti mouse-PE | Isotype control |

In accordance with an embodiment of the present invention, immunohistochemistry staining (IHC) is carried out using the following protocol:

Example 1

IHC Staining Protocol for ACPs

| Slide No. | Staining 1st step | Aim of staining |
|---|---|---|
| | -mIgG1-FITC | Isotype control |
| | mIgG1-PE | Isotype control |
| | CD34-APC | |
| | CD144-FITC | |
| | CD133-PE | |

Example 2

IHC Staining Protocol for CMC Progenitors

| Slide No. | Staining 1st step | Staining 2nd step | Aim of staining |
|---|---|---|---|
| 1. | -mIgG1 | mIgG1-FITC | Isotype control |
| 2. | mIgG1 | Anti mouse-Cy-3 | Isotype control |
| 3. | Connexin 43 | Anti mouse-FITC | |
| 4. | Alfa actin | Anti mouse-FITC | |
| 5. | Troponin | Anti mouse-PE | |

In accordance with an embodiment of the present invention, a tube formation assay is carried out using the following protocol:

Tube formation was tested using the ECM625 (Chemicon) in vitro angiogenesis assay kit.

Angiogenic pattern and vascular tube formation was numerically scored as described by Kayisli U. A. et al. 2005 (52).

In accordance with an embodiment of the present invention, secretion of cytokines from harvested cells is assessed using the following protocol:

Culture 0.5–1×10^6 cells/ml over night in 24 well plates in serum-free medium (e.g., X-vivo 15)

Collect culture supernatant and spin at 1400 rpm for 5 minutes

Transfer supernatant to an eppendorf tube and freeze at −80° C. until ready to test cytokine secretion.

Example no. 1

ELISA for IL-8

A commercial DuoSet CXCr8/IL-8 (R&D Systems) was used for the detection of IL-8 secretion.

Example no. 2

Cytometric Bead Array

A commercial cytometric bead array (CBA) kit for human angiogenesis (BD 558014) was used for the detection of IL-8, VEGF, TNF and Angiogenin secretion.

For some applications, techniques described herein are practiced in combination with techniques described in one or more of the references cited in the present patent application. All references cited herein, including patents, patent applications, and articles, are incorporated herein by reference.

It is to be appreciated that by way of illustration and not limitation, techniques are described herein with respect to cells derived from an animal source. The scope of the present invention includes performing the techniques described herein using a CCP derived from non-animal cells (e.g., plant cells), mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method for obtaining a progenitor/precursor cell population comprising cardiomyocyte precursor cells (CMCs) comprising:
   i. applying cells from blood or hematopoietic source to a density gradient and selecting a population of cells that have density of less than 1.072 g/ml,
   ii. subjecting the cells with density of less than 1.072 g/ml to cell sorting and selecting a core cell population (CCP) of at least 5 million cells of which at least 1% are CD34+ CD45−/dim, and wherein at least 30% of the cells of the CCP are CD14+; and
   iii. in vitro stimulating the CCP by culturing the CCP in the presence of:
      (a) one or more growth factors selected from the group consisting of: bFGF, TGF-beta, EGF, IGF, PDGF, and VEGF, and
      (b) dexamethasone to differentiate the CCP into a progenitor/precursor cell population (PCP),
   wherein at least some of the progenitor/precursor cell population includes cardiomyocyte precursor cells (CMCs), the CMCs comprising cells that are positive for one or more molecules selected from the group consisting of: CD31, CD117, cardiac troponin, connexin 43, desmin, α-actin, and β-actin.

2. The method according to claim 1, wherein at least 60% of cells in the CCP are CD31+, and wherein stimulating the CCP comprises stimulating the CCP of which at least 60% of cells therein are CD31+.

3. The method according to claim 1, comprising preparing the PCP as a product for administration to a patient.

4. The method according to claim 1, comprising preparing the PCP as a research tool.

5. The method according to claim 1, wherein obtaining the CCP from the selected source comprises deriving the CCP from peripheral blood.

6. The method according to claim 1, wherein obtaining the CCP from the selected source comprises deriving the CCP from frozen tissue.

7. The method according to claim 1, wherein stimulating the CCP comprises culturing the CCP in a culture medium comprising a factor selected from the list consisting of: anti-Tie-2, anti-CD133, and anti-CD117.

8. The method according to claim 1, comprising preparing the CCP, and facilitating a diagnosis responsive to a characteristic of the preparation of the CCP.

9. The method according to claim 1, comprising freezing the CCP prior to stimulating the CCP.

10. The method according to claim 1, comprising freezing the PCP.

11. The method according to claim 1, comprising transporting the CCP to a site at least 10 km from a site where the CCP is first created, and stimulating the CCP at the remote site.

12. The method according to claim 1, comprising transporting the PCP to a site at least 10 km from a site where the PCP is first created.

13. The method according to claim 1, comprising identifying the PCP as being suitable for therapeutic implantation in response to an assessment that the PCP includes at least 1 million PCP cells.

14. The method according to claim 1, comprising identifying the PCP as being suitable for therapeutic implantation in response to an assessment that at least 1.5% of cells of the PCP demonstrate a feature selected from the list consisting of: a desired morphology, a desired cellular marker, a desired cellular component, a desired enzyme, a desired receptor, a desired genotypic feature, and a desired physiological feature.

15. The method according to claim 1, further comprising selecting the PCP that comprises at least 1 million angiogenic cell precursors (ACPs) thereby identifying the PCP as being suitable for therapeutic implantation.

16. The method according to claim 1, comprising identifying the PCP as being suitable for therapeutic implantation in response to an assessment that the PCP includes at least 1 million cardiomyocyte progenitors.

17. The method according to claim 1, further comprising characterizing the PCP as including angiogenic cell precursors (ACPs) by evaluating the PCP cells using a phenotypical feature of cells in the PCP, a genotypical feature of cells in the PCP, and a physiological feature of cells in the PCP.

18. The method according to claim 17, wherein characterizing the PCP further comprises assessing secretion by the PCP of a molecule selected from the list consisting of IL-8, angiogenin, VEGF, MMP2, and MMP9.

19. The method according to claim 17, wherein characterizing the PCP comprises assaying the cells for presence of a marker selected from CD31, CD34, CD117, CD133, Tie-2, CD34+CD133+, KDR, CD34+KDR+, CD144, von Willebrand Factor, SH2 (CD105), SH3, fibronectin, collagen type I, collagen type III, collagen type IV, ICAM type 1, ICAM type 2, VCAM1, vimentin, BMP-R IA, BMP-RII, CD44, integrin b1, aSM-actin, MUC18, and CXCR4, wherein the presence of the marker if indicative of PCP as including ACPs.

20. The method according to claim 18, wherein characterizing the PCP comprises identifying that at least 1.5% of cells of the PCP have the selected marker.

21. The method according to claim 18, wherein characterizing the PCP comprises measuring the uptake of Ac-LDL by the PCP.

22. The method according to claim 18, wherein characterizing the PCP comprises culturing a portion of the PCP on a semi-solid extracellular matrix (ECM), and identifying in the cultured portion a feature selected from the list consisting of: a tube-like structure, a colony, a cluster, and a tendency to migrate towards a chemoattractant.

23. The method according claim 1, comprising characterizing the PCP as including a cardiomyocyte (CMC) PCP in response to an evaluation of a feature selected from the list consisting of: a phenotypic feature of cells in the PCP, a genotypic feature on the cells in the PCP, and a physiological feature of cells in the PCP.

24. The method according to claim 23, wherein characterizing the PCP comprises characterizing the PCP in response to identification in the PCP of an action in response to activation of the PCP, the action selected from the list consisting of: increasing intracellular $Ca^{2+}$ level, generating membranal electrophysiological action potentials, and mechanical cellular contraction in vitro.

25. The method according to claim 1, comprising facilitating a diagnosis responsive to stimulating the CCP to differentiate into the PCP.

26. The method according to claim 1, wherein the stimulating further comprises incubating the CCP in a container having a surface comprising a growth-enhancing factor.

27. The method according to claim 26, wherein the growth-enhancing factor is selected from the list consisting of: collagen, plasma, fibronectin, a growth factor, tissue-derived extra cellular matrix, and an antibody to a stem cell surface receptor.

28. A method for obtaining a progenitor/precursor cell population comprising cardiomyocyte precursor cells (CMCs) comprising:
    (i) applying cells from blood or hematopoietic source to a density gradient and selecting cells with density of less than 1.072 g/ml;
    (ii) subjecting the cells with density of less than 1.072 g/ml to cell sorting and selecting a core cell population (CCP) of at least ten thousand cells that have a density of less than 1.072 g/m, wherein at least 30% of the cells of the CCP are CD14+, by selecting cells from blood or a hematopoietic source with a density gradient, wherein cells with density of less than 1.072 g/ml are selected; and
    (iii) in vitro stimulating the CCP by culturing the CCP in the presence of:
    (a) one or more growth factors selected from the group consisting of: bFGF, TGF-beta, EGF, IGF, PDGF, and VEGF, and
    (b) dexamethasone to differentiate the CCP into a progenitor/precursor cell population (PCP),
    wherein at least some of the PCP includes cardiomyocyte precursors (CMCs), the CMCs having cells that are positive for one or more molecules selected from the group consisting of: CD31, CD117, cardiac troponin, connexin 43, desmin, α-actin, and β-actin.

* * * * *